(12) United States Patent
Waterson et al.

(10) Patent No.: US 9,208,287 B2
(45) Date of Patent: Dec. 8, 2015

(54) SYSTEM AND METHOD FOR REMOTE TELE-HEALTH SERVICES

(71) Applicants: Vincent Waterson, Ventura, CA (US); David Sturgess, Chesterfield (GB)

(72) Inventors: Vincent Waterson, Ventura, CA (US); David Sturgess, Chesterfield (GB)

(73) Assignee: VIDEOKALL, INC., Potomac, MD (US)

( * ) Notice: Subject to any disclaimer, the term of this patent is extended or adjusted under 35 U.S.C. 154(b) by 0 days.

(21) Appl. No.: 14/098,223

(22) Filed: Dec. 5, 2013

(65) Prior Publication Data

US 2014/0095196 A1 Apr. 3, 2014

Related U.S. Application Data

(63) Continuation-in-part of application No. 12/987,618, filed on Jan. 10, 2011.

(60) Provisional application No. 61/873,179, filed on Sep. 3, 2013, provisional application No. 61/889,410, filed on Oct. 10, 2013.

(51) Int. Cl.
| | |
|---|---|
| *A61B 5/00* | (2006.01) |
| *A61B 7/00* | (2006.01) |
| *A61B 7/04* | (2006.01) |
| *G06F 19/00* | (2011.01) |
| *G06Q 10/10* | (2012.01) |
| *G06Q 50/22* | (2012.01) |

(52) U.S. Cl.
CPC ........ *G06F 19/3418* (2013.01); *G06F 19/3425* (2013.01); *G06F 19/366* (2013.01); *G06Q 10/10* (2013.01); *G06F 19/3456* (2013.01); *G06Q 50/22* (2013.01)

(58) Field of Classification Search
CPC . G06F 19/3418; G06F 19/34; G06F 19/3406; G06G 19/345
USPC .................. 705/2, 3, 4; 600/300, 586; 381/67
See application file for complete search history.

(56) References Cited

U.S. PATENT DOCUMENTS

| | | | |
|---|---|---|---|
| 5,441,047 A | 8/1995 | David et al. | |
| 6,501,981 B1* | 12/2002 | Schweikard et al. | 600/427 |
| 7,329,226 B1* | 2/2008 | Ni et al. | 600/529 |
| 7,578,969 B2 | 8/2009 | Mielnik et al. | |
| 7,593,030 B2 | 9/2009 | Wang et al. | |
| 7,650,291 B2 | 1/2010 | Rosenfeld et al. | |
| 7,674,436 B1 | 3/2010 | Feldman et al. | |

(Continued)

*Primary Examiner* — Sheetal R Paulson
*Assistant Examiner* — John Go
(74) *Attorney, Agent, or Firm* — Drinker Biddle & Reath LLP

(57) ABSTRACT

A tele-health services cabin includes a plurality of vital signs monitoring devices, a cabin management unit, and videoconferencing hardware via which a remote practitioner in a remote medical call center videoconferences with a patient in the cabin to diagnose symptoms of the patient. The cabin management unit includes a processor that controls the cabin, a data input at which patient data is provided from the vital signs monitoring devices, and a transmitter connectable to a communication link for bi-directional communication between the cabin management unit and the medical call center, where the transmitter transmits the patient data to the medical call center. The tele-health services cabin may include a patient chair including a motorized seat back and at least one sensor encapsulated in the seat back. The tele-health services cabin may include a hands-free medical device station. The tele-health services cabin may include an automatic cleaning system.

6 Claims, 20 Drawing Sheets

(56) References Cited

U.S. PATENT DOCUMENTS

| | | |
|---|---|---|
| 7,778,852 B2 | 8/2010 | Vasko et al. |
| 2001/0026162 A1* | 10/2001 | Nagai ................ B60N 2/002 |
| | | 324/687 |
| 2002/0120199 A1* | 8/2002 | Ogura et al. ................ 600/485 |
| 2004/0220464 A1 | 11/2004 | Benninger et al. |
| 2004/0260156 A1* | 12/2004 | David ................ A61B 5/0205 |
| | | 600/300 |
| 2005/0128091 A1 | 6/2005 | Ricci |
| 2005/0171451 A1* | 8/2005 | Yeo et al. ................ 600/547 |
| 2005/0265606 A1* | 12/2005 | Nakamura ................ 382/218 |
| 2006/0015027 A1* | 1/2006 | Matthews .......... A61B 5/04085 |
| | | 600/393 |
| 2006/0041196 A1 | 2/2006 | Matthews et al. |
| 2006/0285696 A1* | 12/2006 | Houtsma ................ A61B 7/04 |
| | | 381/67 |
| 2007/0239395 A1* | 10/2007 | Jenkins et al. ................ 702/158 |
| 2008/0004540 A1 | 1/2008 | Nakao et al. |
| 2008/0077435 A1* | 3/2008 | Muradia ............. G06F 19/3418 |
| | | 705/2 |
| 2008/0139893 A1* | 6/2008 | Lee et al. ................ 600/300 |
| 2009/0011836 A1 | 1/2009 | Friesen et al. |
| 2009/0066486 A1 | 3/2009 | Kiekbusch et al. |
| 2009/0137882 A1* | 5/2009 | Baudino et al. ................ 600/301 |
| 2009/0223635 A1 | 9/2009 | Lawless |
| 2010/0130808 A1* | 5/2010 | Hattori ................ 600/9 |
| 2010/0141910 A1 | 6/2010 | Van Der Heijden et al. |
| 2010/0166269 A1* | 7/2010 | Logan et al. ................ 382/128 |
| 2010/0222649 A1 | 9/2010 | Schoenberg |
| 2011/0021866 A1 | 1/2011 | Iizuka et al. |
| 2011/0034784 A1 | 2/2011 | David et al. |
| 2011/0166465 A1 | 7/2011 | Clements et al. |
| 2012/0130739 A1 | 5/2012 | Crane |

* cited by examiner

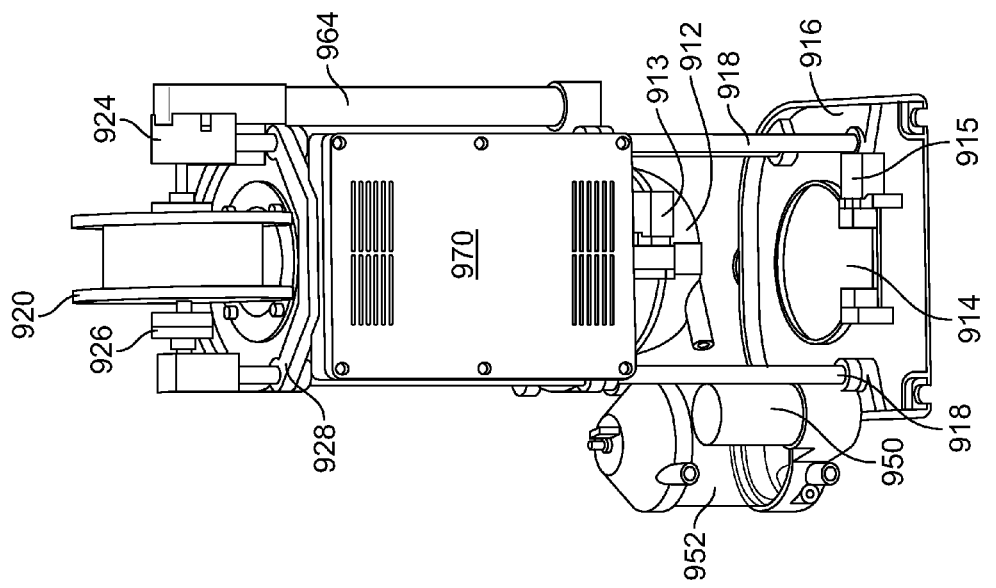
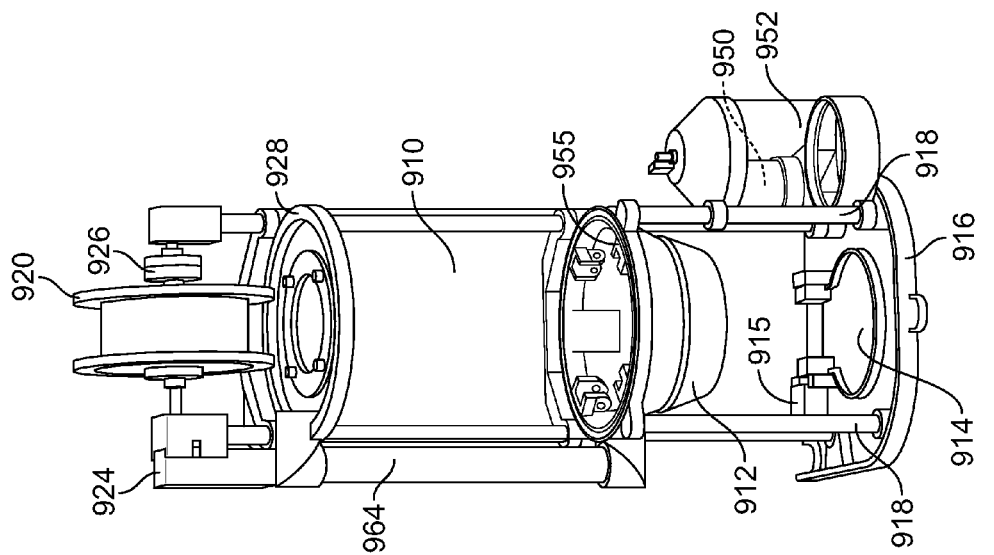

SYSTEM AND METHOD FOR REMOTE TELE-HEALTH SERVICES

CROSS-REFERENCE TO RELATED PATENT APPLICATIONS

This application is a continuation-in-part of U.S. patent application Ser. No. 12/987,618, filed Jan. 10, 2011, and also claims the priority benefit of U.S. Provisional Patent Application No. 61/873,179, filed Sep. 3, 2013, and U.S. Provisional Patent Application No. 61/889,410, filed Oct. 10, 2013, the entire contents of which are incorporated by reference.

BACKGROUND

1. Field

Various embodiments of the invention relate generally to medical health care technology, and more particularly, to providing remote tele-health services.

2. Related Art

Conventional medical services and care are experiencing increased demand as a result of the increasing age of the population. Additionally, medical care is becoming increasingly more expensive and unavailable for a large portion of the population.

Prior Art includes U.S. Patent Application No. 2010/0222649. An engagement is brokered between a consumer and a medical service provider; a request from a user to consult with a medical service provider having a service provider profile that satisfies at least some attributes in a set of attributes that define a suitable service provider is received in a server computer system; an available medical service provider satisfying at least some of the attributes in the set of attributes is identified; a communication channel is provided to establish an electronic, real-time communication between the user and the medical service provider; a measurement from a sensor configured to measure a physiological parameter of the user is received over the communication channel. This method requires the consumer to own vital signs monitoring devices and be proficient in their use and to also have access to a broadband internet system and own a computer with interfaces which will support connection of these devices.

Prior Art includes U.S. Pat. No. 5,441,047. An ambulatory (in the home) user health monitoring system is disclosed wherein the user is monitored by a health care worker at a central station, while the user is at a remote location. The user may be a person having a specific medical condition monitored or may be an elderly person desiring general medical surveillance in the home environment. Cameras are provided at the user's remote location and at the central station such that the user and the health care worker are in interactive visual and audio communication. A communications network such as an interactive cable television is used for this purpose. Various medical condition sensing and monitoring equipment are placed in the user's home, depending on the particular medical needs of the user. The user's medical condition is measured or sensed in the home and the resulting data is transmitted to the central station for analysis and display. The health care worker then is placed into interactive visual communication with the user concerning the user's general well-being, as well as the user's medical condition. Thus, the health care worker can make "home visits" electronically, twenty-four hours a day.

Prior Art includes U.S. Pat. No. 7,778,852. A remotely programmable and accessible medical device system including an interface unit and a medical device connected to a user is disclosed. Through a transceiver, such as a telephone or computer, a person may obtain status reports from a remotely located medical device in audible, electronic or paper form. In addition, the person may change a protocol associated with the medical device or be alerted at a remote location of an alarm associated with the medical device.

A conventional medical device, such as a blood glucose monitor, is designed to be held in the hand by a user. The user lances a finger to draw a small amount of blood, which is applied to a disposable glucose test strip previously inserted into the monitor by the user. The results are displayed on a screen on the monitor and may also be sent via data cable to a computer for archive. The conventional blood glucose monitor cannot be used without handling by a user so that in an unmanned micro clinic it would not be possible to determine if the last user properly cleaned the monitor, using for example a medicated wipe. A medical device, which is visibly dirty (e.g., portions of the device covered in chocolate, grease from food, dirt, etc.) may be so uninviting to the next user that the user would not wish to clean the device manually, and so the device would need to cleaned automatically.

Automatic cleaning systems would require the blood glucose monitor to be immersed or sprayed with a liquid disinfectant. The receptacle in the monitor which accepts the test strip, however, cannot be immersed or sprayed with a disinfectant.

In view of the foregoing there is need for systems for providing affordable and accessible health care. What is needed is a remotely accessed tele-health system providing a plurality of vital signs monitoring devices in a secure, sanitized public access cabin connected to a Medical Call Center (MCC). Users of a tele-health system may be provided with convenient and affordable access to primary healthcare without having to travel a significant distance for care.

SUMMARY

In an embodiment, tele-health services cabin includes a plurality of vital signs monitoring devices, a patient chair including a motorized seat back and at least one sensor encapsulated in the seat back, a cabin management unit, and videoconferencing hardware via which a remote practitioner in a remote medical call center videoconferences with a patient in the cabin to diagnose symptoms of the patient. The cabin management unit includes a processor that controls equipment in the cabin, a data input at which patient data is provided from the vital signs monitoring devices, a data output to control the vital signs monitoring devices, and a transmitter connectable to a communication link for bi-directional communication between the cabin management unit and the medical call center, where the transmitter transmits the patient data to the medical call center.

The plurality of vital signs monitoring devices may include a stethoscope and a height measurement device. The at least one sensor encapsulated in the seat back may be communicatively coupled to the stethoscope. The motorized seat back may include at least actuator that moves the at least one sensor to a position corresponding to a position of the patient's lungs.

The processor may determine the position of the patient's lungs using the following formulas:

$$V = (B^*R) + (B^*Zv(S,A));$$

$$H = B^*Zh(S,A);$$

where V is a vertical lung center V, H is a lung height, B is the seated height of the patient, S is the gender of the patient, R is a normal lung center location as a fraction of seated height, Zv is a table of vertical factors, and Zh is a table of gender factors.

In an embodiment, the at least one sensor encapsulated in the seat back includes a stethoscope, and the motorized seat back includes at least one actuator that moves the stethoscope to a position corresponding to a position of the patient's lungs.

A method in a tele-health services cabin includes receiving the gender of a patient, measuring a seated height of the patient while the patient is seated in a patient chair, analyzing, using a processor, a position of the patient's lungs based on the patient's gender and seated height, and positioning at least one sensor encapsulated in a seat back of the patient chair to an initial position that is aligned with analyzed position of the patient's lungs.

The analyzing step may include calculating a vertical lung center V and a lung height H of the patient using the following formulas:

$$V=(B*R)+(B*Zv(S,A));$$

$$H=B*Zh(S,A);$$

where B is the seated height of the patient, S is the gender of the patient, R is a normal lung center location as a fraction of seated height, Zv is a table of vertical factors, and Zh is a table of gender factors.

The method may further include receiving a command from a remote medical call center to move the at least one sensor, and repositioning the sensor based on the received command.

In another embodiment, a tele-health services cabin includes a medical device station, a cabin management unit, and videoconferencing hardware via which a remote practitioner in a remote medical call center videoconferences with a patient in the cabin to diagnose symptoms of the patient. The medical device station includes an enclosure having a wall, where an opening is formed in the enclosure wall, and a medical device disposed behind the enclosure wall, where a test strip receptacle of the medical device is aligned with the opening. The cabin management unit includes a processor that controls equipment in the cabin, a data input at which patient data is provided from the medical device, a data output to control the vital signs monitoring devices, a transmitter connectable to a communication link for bi-directional communication between the cabin management unit and the medical call center, wherein the transmitter transmits the patient data to the medical call center.

The opening formed in the enclosure wall may be sized to allow a test strip to be inserted into the test strip receptacle of the medical device.

The medical station may further include a bracket having a first movable arm, where the medical device is mounted on the first movable arm in a horizontal plane in the enclosure. The first movable arm may be operable to retract the medical device away from the enclosure wall and to rotate the medical device.

The bracket may further include a second movable arm operable to press an eject button of the medical device.

In various embodiments, the medical device may be a blood glucose monitor or a cholesterol monitor.

In still another embodiment, a tele-health services cabin includes an automatic cleaning system, a cabin management unit, and videoconferencing hardware via which a remote practitioner in a remote medical call center videoconferences with a patient in the cabin to diagnose symptoms of the patient. The automatic cleaning system includes a cleaning chamber and at least one spray nozzle disposed in an interior of the cleaning chamber. The cabin management unit includes a processor that controls the equipment in the cabin, a data input at which patient data is provided from a medical device, a data output to control the medical device, and a transmitter connectable to a communication link for bi-directional communication between the cabin management unit and the medical call center, where the transmitter transmits the patient data to the medical call center.

The automatic cleaning system may further include a winch having a motor and a cable spool or pulley disposed above the cleaning chamber, a cable wound around the spool, where one end of the cable may be connected to the medical device and the other end of the cable may be communicatively coupled to the cabin management unit. The medical device may be suspended in the cleaning chamber via the cable.

The cable may be routed over the top of the cleaning chamber by a driven pulley and then looped over idler pulleys and counter weight to form a "U"-shaped loop of cable in a cable shaft. One end of the cable may be connected to external power and communications.

The automatic cleaning system may further include a first bowl-shaped flap hingedly disposed at a bottom of the cleaning chamber, a first actuator operable to open and close the first flap, a base plate disposed below the bottom of the cleaning chamber, the base plate having a second flap hinged disposed thereon, a second actuator operable to open and close the second flap, and a locking mechanism to lock the first flap and the second flap closed.

The automatic cleaning system may further include a wash cycle reservoir connected to the at least one spray nozzle, a wash cycle pump that pumps cleaning solution from the wash cycle reservoir to the at least one spray nozzle, and a drain pipe coupled to the first flap and the wash cycle reservoir to drain cleaning solution from the cleaning chamber back into the wash cycle reservoir.

The automatic cleaning system may further include a primary reservoir connected to the wash cycle reservoir, a clean solution pump that pumps clean cleaning solution from the primary reservoir to the wash cycle reservoir, a first pipe coupled to the wash cycle pump and the at least one spray nozzle, where the wash cycle pump receives cleaning solution from the wash cycle reservoir and feeds the cleaning solution through the first pipe to the at least one spray nozzle, and a second pipe coupled to the cleaning chamber and the wash cycle reservoir to return run-off cleaning solution from the cleaning chamber back to the wash cycle reservoir.

The wash cycle reservoir may hold an amount of cleaning solution sufficient for one cleaning cycle. The wash cycle reservoir may include an outlet to dispose of used cleaning solution to a waste solution reservoir. The automatic cleaning system may further include a filter disposed at an inlet to the wash cycle pump to collect debris, where the collected debris on the filter is cleared when the used cleaning solution is disposed to the waste solution reservoir.

The cleaning solution may include water, microbial disinfectants, and detergents.

The automatic cleaning system may further include an air drying system. The air drying system may include an intake fan that draws ambient air into the air drying system, a heater configured to heat ambient air from the intake fan and to deliver heated air or ambient temperature air to the interior of the cleaning chamber.

The processor of the cabin management unit may be configured to deliver the medical device to within arms-reach of a user, measure an amount of cleaning solution required to clean the medical device, determine whether the medical device has been used and requires cleaning, determine when to retract the medical device to a predetermined location at the top of the cleaning chamber, determine whether the medical device is retracted into the interior of the cleaning chamber, determine whether a primary reservoir has sufficient amount of cleaning solution for a wash cycle, determine whether a waste reservoir has sufficient capacity to hold waste from a wash cycle, determine when to close and lock a first flap of the cleaning chamber, determine when to close and lock a second flap of a base plate disposed below the cleaning chamber, determine when to pump cleaning solution from the primary reservoir to a wash cycle reservoir, determine when to pump cleaning solution from the wash cycle reservoir to the at least one spray nozzle to decontaminate the medical device, run the wash cycle for a predetermined amount of time, run the drying cycle for a predetermined amount of time, and determine when to dispose of used solution to a waste solution reservoir.

BRIEF DESCRIPTION OF THE DRAWINGS

Various embodiments of the invention are described in more detail below with reference to the embodiments illustrated in the drawings, in which:

FIGS. 10A-10D are various views of an automatic cleaning system for a tele-health cabin, according to an embodiment.

DETAILED DESCRIPTION OF THE EMBODIMENTS

Figure 1:
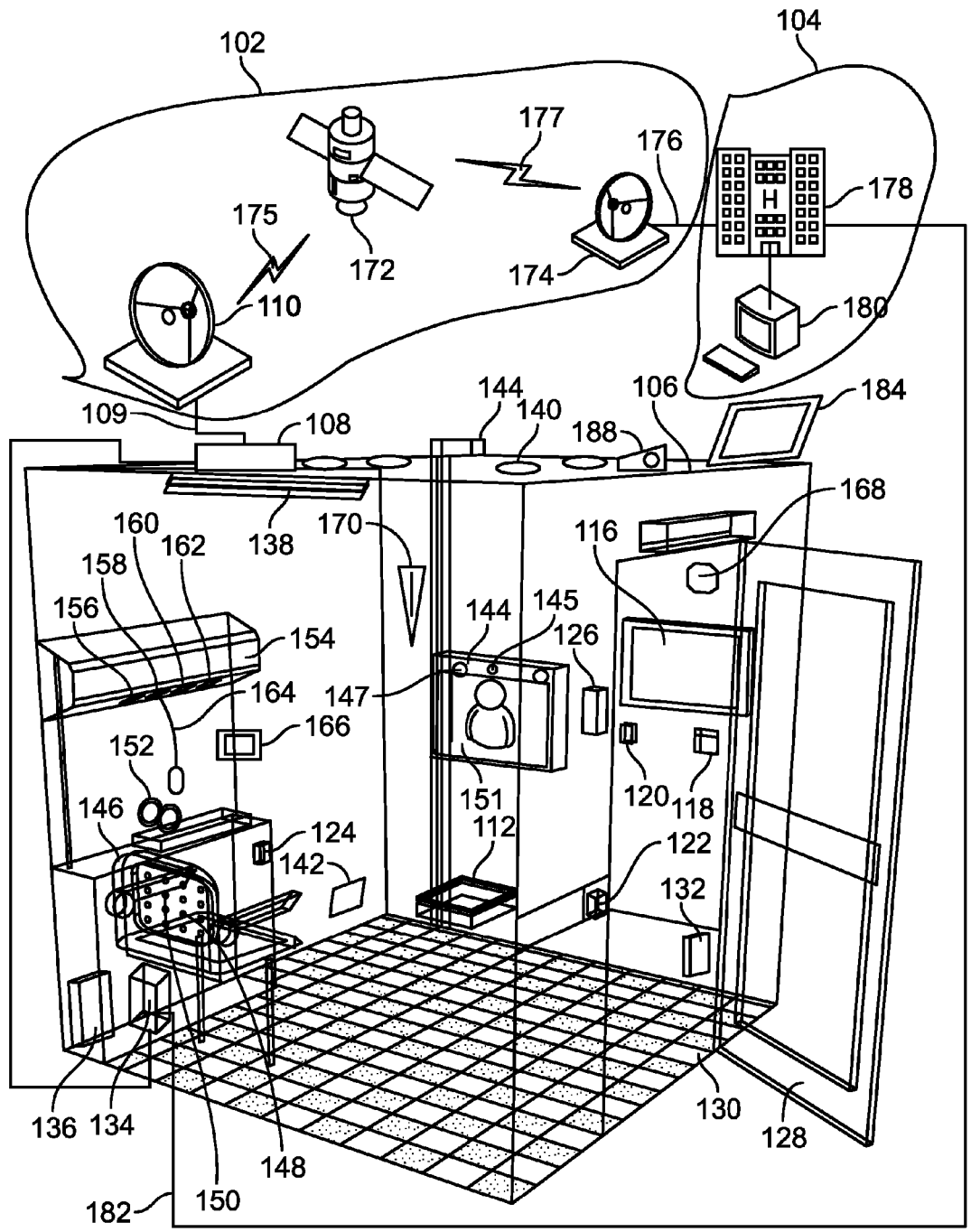
FIG. 1 is a perspective view illustrating a tele-health cabin and system, according to an embodiment.

A description of various illustrative embodiments of the invention follows.

A first embodiment will be described which provides means and methods for providing affordable health care service. User visit automation and efficient management of expensive medical personnel resources may be provided in order to reduce inefficiencies and waste in current healthcare systems. For example, efficiencies may be realized via outpatient services. Tele-health services may be provided for users to access on a "walk-in" basis. Furthermore, users may be provided access to a public tele-health cabin in order to benefit from efficiencies enabled by a digital healthcare system. Users may be provided access to a large pool of medical professionals via remote medical call centers. The fusion of satellite communications, advanced telemedicine devices and bi-directional video communications provided by tele-health cabins may be provided via convenient access areas, such as supermarkets or gas stations. Furthermore, tele-health cabins may provide affordable health care to the public at large.

In other embodiments, a mobile vehicle equipped with a video terminal and satellite communications capabilities may be maneuvered to remote areas providing medical care in geographic regions not capable of supporting independent medical personnel.

In yet other embodiments, tele-health cabin units may be located in areas or facilities providing senior members of society with convenience, travel cost savings, and economical healthcare.

An unmanned, cost effective walk-in tele-health cabin may be provided for enabling users to remotely consult with trained medical staff for a variety of common outpatient symptoms.

Tele-health devices and communications traffic engineering of call center staff may be provided in order for a multiplicity of users to communicate and collaborate with a finite resource of medical professionals. Benefits may include early detection and treatment of illness on a scale as to potentially reduce associated outpatient care costs. Furthermore, aggregate annual healthcare costs may be reduced by an associated reduction in the quantity of people visiting hospital emergency rooms for treatment for minor ailments. Tele-health cabins may be provided for wheelchair access and may be located in geographically convenient areas. Non-limiting examples of convenient locations include pharmacies located in supermarkets for more populated regions and in gas stations and other convenience retail establishments for rural populations. The service may also be provided using satellite to passengers and/or crew of ocean going vessels.

A telecommunications link may be defined as a "routable and switched" digital data connection which may operate to enable a remote consultation session to be established between a tele-health cabin and one of a multiplicity of terminals geographically located at one of a number of MCCs. A bi-directional communication channel may be established with sufficient bandwidth to carry data for a digital video conference between user/patient and health care provider. Furthermore, information may be simultaneously communicated for the various instruments and for other controlling functions. Non-limiting examples of communication methods include satellite, optical fiber, copper wires and other methods for communicating information bi-directionally. A connection may be established at the initiation of a consultation session, identified by insertion of a card device into a card terminal. A connection may also be established using a cellphone or other wireless devices such as an iPad. Furthermore, a session may be terminated by the removal of a card device.

In other embodiments, tele-health cabins may be provided for users seeking primary healthcare where users may connect to hospital-based MCCs via a bi-directional telecommunications link where qualified nurse practitioners, doctors and other medical practitioners may provide face-to-face tele-health consultations.

Users of tele-health cabins may be provided with access to a multiplicity of vital signs monitors connected via bi-directional telecommunications video collaboration to staff geographically located at a MCC who may operate to analyze the user's/patient's health.

Tele-health cabins may be provided with a footprint small enough such that the tele-health cabins may be located in a supermarket or other convenient retail establishment. Furthermore, the footprints of tele-health cabins may be configured small enough such that valued retail space may not be compromised. Furthermore, tele-health cabins may be of sufficient size to accommodate up to two persons. Furthermore, tele-health cabins may provide a pre-sanitized sound reducing enclosure for ensuring a healthy environment while providing complete privacy during video consultations.

In still other embodiments, a system may be provided for linking tele-health cabins via a telecommunications channel with one or more regional hospitals or medical clinics. Furthermore, this structure may operate to provide facilities and medical personnel for providing MCC services per the specified needs of a particular user/patient.

In other embodiments of the present invention, primary health care services may be provided via tele-health cabins located in rural environments where it may not be viable to provide a mobile or fixed clinic staffed by medical personnel.

Tele-health services may be provided via supermarkets having pharmacies located in or adjacent to the supermarkets. Furthermore, tele-health services may be provided in geographically rural locations such as fire, ambulance or gas stations.

As an example, tele-health cabins may be situated in about 30 square feet of area. Furthermore, tele-health cabins may be acoustically insulated and provide equipment for a video conference terminal, a card device terminal, a multiplicity of vital signs monitors and a communication connection for a telecommunications link. A tele-health cabin may be equipped with a sanitization system for continually sanitizing the air and surfaces interior to the tele-health cabin. Furthermore, tele-health cabins may be configured for support of wheelchair access.

Services provided via tele-health cabins may be charged against a pre-paid card device. Card devices may be configured based upon a time required for service or based upon the type of service rendered.

Tele-health cabins may be equipped with a multiplicity of devices for measuring a user's/patient's vital signs. Non-limiting examples of devices for measuring vital signs include blood pressure, temperature and weight. Disposable probes may be provided for making contact with the various devices associated with a tele-health cabin. Tele-health cabins may operate unattended. Furthermore, users/patients of a tele-health cabin may operate to generate connections with vital sign monitors to their person under instructions from a medical professional who may be geographically located at a remote MCC.

Users seeking to use tele-health services may purchase a card device provided via convenient retail establishments. Non-limiting examples of retail establishments include supermarkets and gas stations. Furthermore, users may purchase disposable probes located at convenient retail establishments for later attachment to the tele-health equipment.

Users may opt to pay for a minimum consultation fee or purchase additional consultation time.

Users may initiate tele-health service using an e-check-in terminal located external to tele-health cabins. A user may insert a card device into an e-check-in terminal positioned on the exterior of the tele-health cabin. Furthermore, a user may enter personal medical information via a touch screen in response to an electronic questionnaire provided via a terminal device. Furthermore, a user may operate to use a code reader located near the e-check-in terminal in order to scan codes located on their prescription containers. Furthermore, prescription information may be stored on a user's/patient's card device.

Following completion of an electronic form provided via an e-check-in terminal, a user may be advised to enter tele-health cabin for services or a user may be advised to wait for the next available consultation. Furthermore, a user may be notified of an estimated wait time. Furthermore, a user may be notified with a recommendation to retrieve a paging device located in a nearby dispenser. Furthermore, a user may be notified via an external display and/or a paging device of the availability of a tele-health cabin.

Tele-health cabins may provide equipment for enabling an automated ultraviolet ion process for sanitizing the air and exposed surfaces associated with a tele-health cabin.

After entering a tele-health cabin, users/patients may sit on a seat located in front of a video conference device. Video conference device may be located on a wall adjacent to the entrance door. A user/patient may insert a card device associated with the video phone for initiating a video communications link with an MCC. Furthermore, associated user/patient medical details retrieved from the card device may be presented on a terminal geographically located at the MCC. A medical practitioner may then query the user/patient with questions associated with their medical condition. Furthermore, medical practitioner may request user/patient to create physical contact to their person with one or more tele-health devices provided via the tele-health cabin. Devices connected to the user/patient may communicate information via a communications link. Furthermore, communicated information may be displayed on the medical practitioner's display terminal. During the video consultation the medical professional may also conduct a visual examination of the user's extremities using a secondary camera connected to the tele-health cabin management system. Medical practitioner may also inspect the user's/patient's extremities for cuts, bruises etc.

In other embodiments, capabilities may be provided for diagnostic services whereby a color analysis of the user's/patient's face and tongue may be used for performing a preliminary analysis of the user's health via a video consultation with a medical practitioner geographically located at an MCC.

At the termination of a consultation session, a medical professional may take a number of actions. As an example, the medical professional may transmit an electronic prescription to a pharmacy. Furthermore, the pharmacy may be conveniently located adjacent to the tele-health cabin. Furthermore, a copy of the prescription may be transmitted via a telecommunications link to the user's card device. Furthermore, as another example, the medical practitioner may transmit and store requests for additional tests to the user's/patient's card device. Non-limiting examples of additional tests include blood or specimen.

For additional testing, a user may perform testing at a participating testing laboratory where a card device may be inserted into a card terminal in order to transfer test request information to testing service. Following testing, the testing laboratory may transmit the test results to the card device. Furthermore, the test results may be communicated to the MCC via a telecommunications link. Following additional testing, user/patient may visit a tele-health cabin for a follow-up session during which the test results may be retrieved from the card device and transferred to the medical professional geographically located at the MCC for analysis. Alternatively, the medical professional may retrieve the test results communicated previously via a telecommunications link to the MCC.

A medical professional associated with the MCC may also recommend the user/patient receive further health care. As an example, an inoculation may be provided by a pharmacist located in an adjacent pharmacy. Furthermore, the medical professional may determine the user/patient needs further treatment not available via tele-health services and as a result may recommend the user/patient visit another medical professional participating in the tele-health network. Furthermore, the medical professional may determine the user needs urgent medical attention and as a result the medical professional may recommend the user/patient visit a nearby hospital or emergency room. Furthermore, in some situations, the medical practitioner may summon an ambulance to the user's/patient's geographic location.

At the termination of each tele-health visit the system may automatically transfer information to the user's card device. Furthermore, one or more coupons may be transferred to the user's card device for use in purchasing products associated with the user's medical condition (e.g. a coupon for cough mixture). Furthermore, the coupons may be associated with the supermarket or pharmacy associated with the tele-health cabin.

FIG. 1 is a perspective view illustrating a tele-health cabin and system, according to an embodiment.

A tele-health system 100 includes a satellite communications system 102, an MCC 104 and a tele-health cabin 106.

Satellite communications system 102 may operate to provide bi-directional communications between MCC 104, tele-health cabin 106 and other entities (not shown).

Should the cabin be installed in a location without "Uninterruptable Power" then an Uninterruptable Power Supply may be provided to maintain tele-health cabin operation in the event of local power loss.

MCC 104 may operate to provide healthcare services remotely. Non-limiting examples of services provided by MCC 104 include consultations with doctors, nurses and other qualified health care providers.

Tele-health cabin 106 may operate to provide an interface for users in order to receive services remotely. Non-limiting examples of services provided remotely includes health care consultations and other health care services.

Satellite communications system 102 includes a satellite antenna 110, a satellite 172 and a remote satellite teleport 174.

Satellite antenna 110 may operate to communicate bi-directionally with satellite via a communication channel 175. Satellite 172 may operate to communicate bi-directionally with remote satellite teleport 174 via a communication channel 177.

MCC 104 includes a processing system 178 and a remote terminal 180.

MCC 104 may operate to provide reception, transmission and processing of information. Non-limiting example of information processed includes health care information such as blood pressure, height and weight.

Remote terminal 180 may operate to provide a health care provider (not shown) with information associated with processing system 178.

Tele-health cabin 106 includes a satellite transceiver 108, a digital scale 112, a height measurement device 114, a terminal 116, a code scanner 118, a card terminal 120, a card reader 122, a card terminal 124, a vibrating page device 126, a door 128, a floor 130, a sanitization device 132, a cabin management system 134, an air management device 136, a light device 138, a cameras portion 140, an ultraviolet light 142, a video terminal 144, a seat 146, a stethoscope 148, an EKG equipment portion 150, a blood pressure cuff 152, a cabinet 154, a temperature monitor 156, an oximeter 158, a spirometer 160, a glucose monitor 162, a second camera 164, a small monitor 166, a presence detector 168, a coat hanger 170, a video display 184, a panic device 186 and a siren 188.

Video terminal 144 includes a video camera 145, a microphone 147, an audio portion 149 and a video display 151.

Video camera 145 may operate to capture and transmit video information. Microphone 147 may operate to capture and transmit audio information. Audio portion 149 may operate to inform user/patient via an audio means. Non-limiting examples of audio portion 149 include speakers, ear phones and head phones. Video display 151 may operate to present video information to a user/patient located internal to tele-health cabin 106.

Satellite transceiver 108 may operate to communicate bi-directionally with satellite devices. Digital scale 112 may operate to determine and communicate weight information. Height measurement device 114 may operate to determine and provide height information. Non-limiting examples of operational modes for height measurement device 114 includes sonar and laser.

Terminal 116 may operate to present information to a user. Non-limiting examples of uses for terminal 116 includes user/patient consultation initiation and presenting other user/patient associated information. Code scanner 118 may operate to receive and process code information. Non-limiting examples of code scanner 118 include bar code scanner.

Card terminal 120 may operate to receive, transmit and process information for a card device. Non-limiting examples of a card device include smart card, insurance card and driver's license.

Card reader 122 may operate to receive, transmit and process information for a card device. Non-limiting examples of a card device include smart card, insurance card and driver's license.

Card terminal 124 may operate to receive, transmit and process information for a card device. Non-limiting examples of card device include smart card, insurance card and driver's license. Vibrating page device 126 may operate to inform or notify a user or patient of available tele-health cabin 106.

Door 128 may operate to provide a means for allowing entry and for enclosing tele-health cabin 106. Non-limiting examples of door 128 include electromechanically operated door. Floor 130 provides an area for a user to reside and provides a mechanism for performing sanitization. Sanitization device 132 may operate to provide sanitization of tele-health cabin 106.

Cabin management system 134 may operate to communicate with devices and sensors associated with tele-health cabin 106 and may communicate information with MCC 104. Air management device 136 may operate to manage sanitization of tele-health cabin 106. Light device 138 may operate to provide illumination of tele-health cabin 106. Cameras portion 140 may operate to provide detection and communication of unsanitary conditions for floor 130.

Ultraviolet light 142 may operate to provide illumination for cameras portion 140 for determining and communicating unsanitary conditions for floor 130.

Video terminal 144 may operate to display information to a user. Seat 146 may operate to provide user a device for residing in a sitting position. Seat 146 may operate to fold into a compact form. A non-limiting example reason for folding seat 146 to be oriented into compact form includes user access to the features provided by tele-health cabin 106 via a wheel chair.

Stethoscope 148 may operate to determine and communicate acoustic information for medical analysis. Non-limiting examples of types of stethoscope for stethoscope 148 include telephonic and Internet protocol.

EKG equipment portion 150 may operate to determine and communicate electrical heart activity information. Blood pressure cuff 152 may operate to determine and communicate blood pressure information. Cabinet 154 may operate to store equipment and devices when not in use. Temperature monitor 156 may operate to determine and communicate temperature measurements. Non-limiting examples for temperature monitor 156 include infrared. Oximeter 158 may operate to determine and communicate oxygen saturation of blood. Spirometer 160 may operate to determine and communicate air volume as inspired and expired. Glucose monitor 162 may operate to determine and communicate concentration of glucose in blood.

Second camera 164 may operate to provide close-up information for a patient and associated devices. Second camera 164 may be affixed to a flexible boom in order to orient second camera 164 for viewing a user's/patient's body features or equipment associated with tele-health cabin 106 and monitor 166 which allows the patient to position camera 164 to the correct place so that the remote nurse practitioner can instruct the camera 164 to transmit a still image of the desired are of the patient's body to the MCC. Non-limiting examples of information provided include views of patient's skin, blood pressure cuff 152, temperature monitor 156, oximeter 158, spirometer 160 and glucose monitor 162.

Presence detector 168 may operate to determine and communicate the presence or lack presence of a user or patient. Non-limiting examples of uses for presence detector 168 include start of consultation session and end of consultation session. Non-limiting examples of presence detector 168 include motion and infrared.

Coat hanger 170 may operate to provide a location for clothing and for communicating the presence or lack of presence of clothing. Non-limiting examples of uses for coat hanger 170 include notifying a user or patient when an article of clothing should be retrieved from coat hanger 170 following a consultation. As a non-limiting example, coat hanger 170 may operate via a pressure switch.

Video display 184 may operate to receive and present information for external users and patients. Non-limiting examples of information provided includes occupancy status and queue reference number.

Panic device 186 may operate to provide a mechanism for a user or patient to initiate a warning notification. Siren 188 may operate to receive information from panic device 186 for generating a warning notification.

Seat 146 may provide vital signs monitoring devices encapsulated in the seat back. Cabinet 154 may provide storage for vital signs monitoring devices when not in use. Digital scale 112 and height measurement device 114 may be located external to tele-health cabin 106 and may be located in close proximity to terminal 116. Electronic devices and equipment may transmit and receive information from satellite transceiver 108. Satellite transceiver may communicate bi-directionally with satellite antenna 110 via a communication channel 109.

Two way videoconference and data communications may be provided between tele-health cabin 106 and MCC 104 via satellite communications system 102.

Processing system 178 may operate to communicate bi-directionally with remote satellite teleport 174 via a communication channel 176.

A user/patient may operate to initiate and communicate bi-directionally by videoconference call to a medical professional using remote terminal 180.

Alternatively, tele-health cabin 106 and MCC 104 may bypass satellite communications system 102 and communicate bi-directionally via a terrestrial communications network 182.

In operation, a user or patient seeking to receive medical care via tele-health cabin 106 may purchase access. Non-limiting examples of methods for purchasing access include smart card, credit card, debit card and cash. Non-limiting examples of facilities for purchasing access include service desk and kiosk. User or patient may initiate access to medical care via terminal 116. Terminal 116 may be located and accessed external to tele-health cabin 106. User or patient may insert access card into card terminal 120 in order to gain access to tele-health cabin 106. Furthermore, user or patient may enter personal information associated with desired medical treatment via a touch screen provided via terminal 116. Non-limiting examples of information selected by user or patient include language and gender for health care provider.

Furthermore, user or patient may scan, process and communicate bar coded prescription information located on medicine containers via code scanner 118.

Following entry of personal information via terminal 116, a user may remove card device from card terminal 120 and may insert card device into card reader 122. For a determination of a valid card device, door 128 may automatically open via electromechanical means permitting user/patient to enter tele-health cabin 106. Furthermore, following entry of user/patient into tele-health cabin 106, door 128 may automatically close.

Following entry of personal information via terminal 116, a user/patient may be informed via terminal 116 of an occupied or unavailable tele-health cabin 106 and user/patient may be advised to retrieve vibrating page device 126 in order to be notified of the occurrence of an available or vacant tele-health cabin 106. A multiplicity of vibrating page device 126 may be mounted on the wall near door 128. Vibrating page device 126 may operate to enable a user/patient to perform other functions for an occupied or unavailable tele-health cabin 106. Non-limiting examples of other functions which may be performed include shopping and banking. A user/patient making use of vibrating page device 126 may be notified when to return in order to gain access to tele-health cabin 106.

After entering personal information via terminal 116, a user may be presented with a queue reference number for gaining access to tele-health cabin 106. Furthermore, video display 184 may operate to present the queue reference number of the current user/patient being or to be given services via tele-health cabin 106. Furthermore, video display 184 may operate to present a notification of an available tele-health cabin 106 which may be occupied for services.

For a user/patient making use of a wheelchair, door 128 may automatically be operated via an electromechanical means following a user/patient inserting a valid card device into card reader 122. Furthermore, door 128 may automatically close following entry of a user/patient into tele-health cabin 106. Furthermore, a user/patient making user of a wheelchair may rotate the wheelchair in order to position the wheelchair in front of video terminal 144.

A user/patient may initiate service by inserting card device into card terminal 124. An able bodied user/patient may pull down seat 146 for sitting.

An informational video may be displayed via video terminal 144 in order to present user/patient with information associated with the forthcoming virtual consultation.

Information associated with user/patient may be communicated via satellite to a medical practitioner served by MCC 104. Non-limiting examples of information communicated includes audio, video, images and patient vital signs. Video information associated with user/patient may be captured and transmitted via video camera 145. Audio information associated with user/patient may be capture and transmitted via microphone 147.

Software may operate to process information for generating tele-health three-dimensional wire-frame figure which may be displayed as a PIP (Picture in Picture) image on remote terminal 180 of MCC 104. Non-limiting examples of information used for generating three-dimensional wire-frame figure include data retrieved from card device and data retrieved from instrumentation provided by tele-health cabin 106. Three-dimensional wire-frame figure may operate to provide indicators associated with user/patient. Non-limiting examples of indicators include graphically rendering the Body Mass Index (BMI) of the user and, by use of color coding, displaying a color coded representation of areas of the user's or patient's body which may be affected as a result of prescription drugs being consumed. Furthermore, areas of the user's or patient's body associated with a reported ailment may be presented.

Following the viewing of an informational video presented via video terminal 144, a videophone call may automatically be established between user/patient via video terminal 144 and medical practitioner via remote terminal 180 of MCC 104.

During a videophone call a medical practitioner may request a user/patient orient second camera 164 for viewing portions of a user's/patient's skin or other body features and the patient may use monitor 166 to position camera 164 to the correct place. Furthermore, a medical practitioner may request a user/patient attach vital signs monitoring (VSM) devices the user/patient. Non-limiting examples of VSM devices include blood pressure cuff 152, temperature monitor 156, oximeter 158, spirometer 160, and glucose monitor 162. VSM devices may be stored in cabinet 154. Furthermore, VSM devices may be connected via retractable cables enabling easy access, retrieval and storage by user/patient.

A medical practitioner may request a user/patient orient their body position such that the medical practitioner may operate to remotely control the position of the electromechanically operated seat back of seat 146. A medical practitioner may configure seat 146 such that stethoscope 148 and EKG equipment portion 150 make contact through a layer of clothing with the back portion of user/patient.

Data received from one or more VSM devices attached to the user/patient may automatically be transmitted from tele-health cabin 106 via satellite communications system 102 to MCC 104. Furthermore, a medical practitioner may view the received information via remote terminal 180. Non-limiting examples for the received information presented via remote terminal 180 include data overlaid as text and graphics on a three dimensional view of user's/patient's body image.

Following consultation with user/patient, a medical practitioner may perform further actions associated with user/patient residing in tele-health cabin 106. Non-limiting examples of actions performed by medical practitioner include making diagnosis of the health problem for user/patient, transmit medical prescription electronically for the user/patient to a nearby pharmacy, place electronic rendition of prescription on user's/patient's card device, place an electronic rendition of a medical test request on user's/patient's card device, conduct further examinations in follow-up tele-health session(s) and/or refer the user/patient to a participating hospital, clinic or specialist for further treatment. Non-limiting examples of activities a user/patient may perform following a tele-health session include user/patient receiving medications for associated prescriptions received in tele-health session, participating in medical tests via diagnostic laboratory and/or visiting clinic, hospital, etc. for further treatment. Furthermore, results of tele-health session and follow-up activities may be stored on card device.

Sanitization device 132 may operate to perform sanitization of the air located inside tele-health cabin 106 and may operate to perform sanitization of interior surfaces of tele-health cabin 106. Air management device 136 may operate to sanitize air entering tele-health cabin 106. Non-limiting examples for operation of air management device 136 include ultraviolet light irradiating on strips of rare metals. As an example, the air and interior surfaces of tele-health cabin 106 may be sanitized over 30 times per hour in order to minimize the risk of contagious diseases being transmitted between users/patients.

Cameras portion 140, used in conjunction with ultraviolet light 142, may operate to detect a soiled floor 130. Cameras portion 140 may operate to take photographs of cabin floor 130 illuminated via ultraviolet light 142 and detect contaminants. Floor 130 may be printed with a special pattern for enabling detection of contaminants located on floor 130. The contaminant detection system as denoted by cameras portion 140 and ultraviolet light 142 is described in U.S. Provisional Patent Application 61/327,637 previously filed on Apr. 23, 2010 by the applicants for the present application. The contents of this related provisional application are incorporated herein by reference for all purposes to the extent that such subject matter is not inconsistent herewith or limiting hereof.

For detection of a condition of contamination for floor 130 via cameras portion 140 and ultraviolet light 142, a user/patient maybe charged a fee for cleaning tele-health cabin 106. Furthermore, tele-health cabin 106 may operate to notify a third party of tele-health cabin 106 needing cleaning.

In order to prevent interference between light device 138 and video terminal 144, the operational frequency of light device 138 may be dissimilar from the operational frequency of the camera associated with video terminal 144.

Auxiliary power may be provided to light device 138 via an Uninterruptible Power Supply. Uninterruptible Power Supply may operate to maintain power to light device 138 following a power failure.

Cabin management system in conjunction with coat hanger 170 may operate to warn a user/patient in the process of exiting tele-health cabin 106 that the user/patient has not taken their item(s) of clothing with them. Furthermore, cabin management system 134 may also provide a warning notification to MCC 104 regarding the status of coat hanger 170.

Panic device 186 may be activated in an emergency in order to operate siren 188 for summoning assistance from external sources.

Presence detector 168 may be provided in order to detect the condition of a user/patient failing to exit tele-health cabin 106 following a virtual consultation session.

Cabin management system 134 may communicate with equipment and sensors associated with tele-health cabin 106. Furthermore, cabin management system 134 may communicate with MCC 104. Furthermore, remote terminal 180 may receive information from cabin management system 134 associated with equipment and sensors associated with tele-health cabin 106.

A virtual switch may be provided via remote terminal 180 of MCC 104 for enabling a medical professional with the capability to remotely activate door 128. A non-limiting example of a situation where a medical professionally may operate to activate door 128 includes a condition of emergency.

Card device associated with card terminal 120 may operate as a debit or prepaid card in order to charge for services rendered via tele-health cabin 106. Non-limiting examples of services debited from card device include video consultations and other associated consultation fees.

Tele-health cabin 106 may communicate via terrestrial communications network 182 with a database (not shown) of product information associated with commercial establishments hosting tele-health cabin 106. Non-limiting examples of commercial establishments include grocery stores, supermarkets and shopping malls. Tele-health cabin 106 in conjunction with the commercial establishment's database may operate to provide electronic coupons on user's/patient's card device. Coupons provided may be associated with diagnoses related to tele-health cabin 106 consultation. User/patient may view coupons deposited on card device following exit from tele-health cabin 106 by inserting the card device into card terminal 120.

Figure 2:
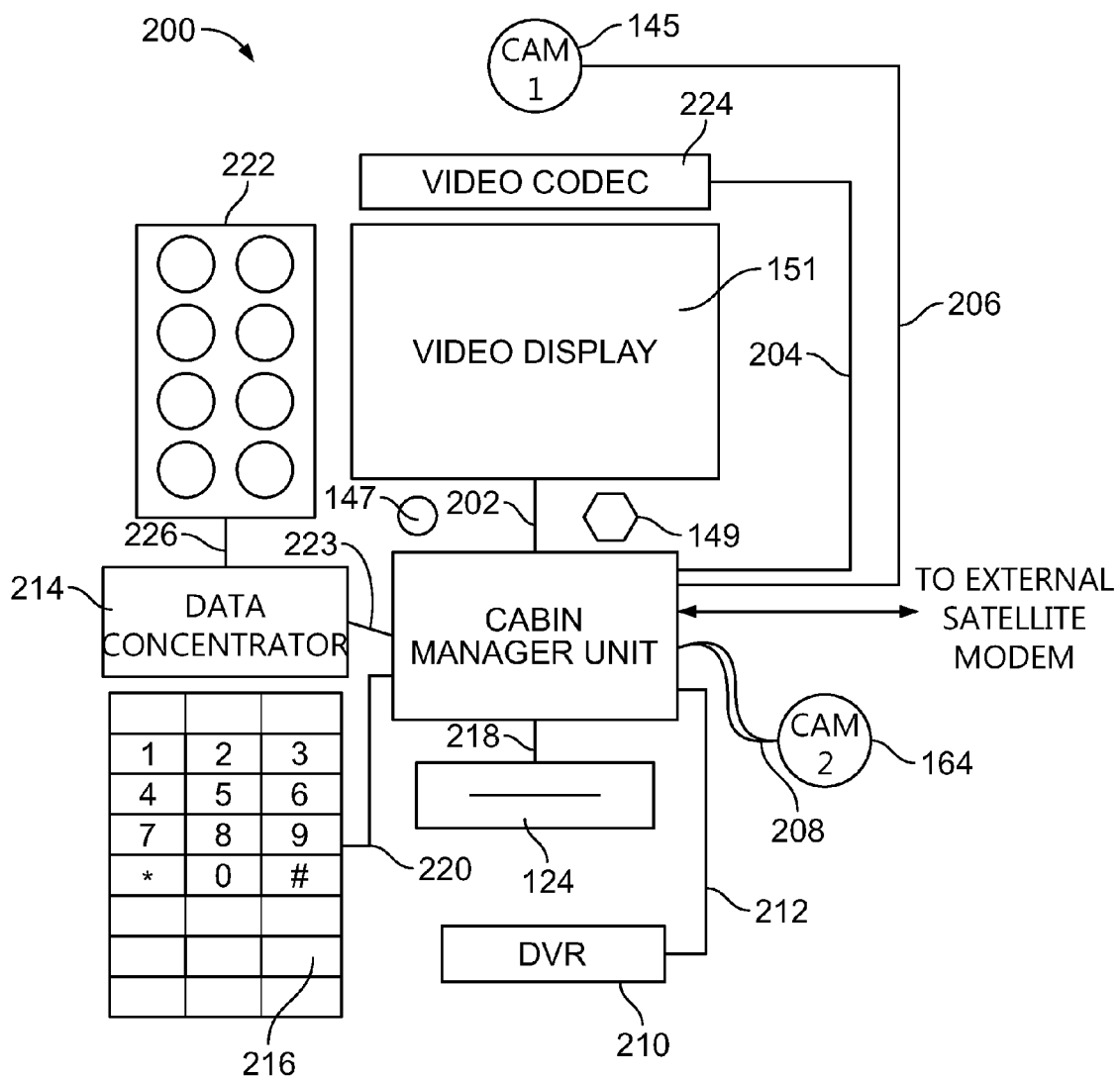
FIG. 2 is a diagram illustrating a system associated with the tele-health cabin shown in FIG. 1, according to an embodiment.

FIG. 2 is a diagram illustrating a system associated with the tele-health cabin 106 of FIG. 1, in accordance with an embodiment.

A system 200 includes card terminal 124 (FIGS. 1-2), cabin management system 134 (FIGS. 1-2), video camera 145 (FIGS. 1-2), microphone 147 (FIGS. 1-2), audio portion 149 (FIGS. 1-2), video display 151, second camera 164 (FIGS. 1-2), a digital recorder 210, a data concentrator 214, a keypad 216, a vital signs portion 222 and a video codec 224.

Digital recorder 210 may operate to record information for later processing and/or use. Non-limiting examples of information recorded via digital recorder 210 include audio and video data.

Data concentrator 214 may operate to process and organize information associated with vital signs for user/patient.

Keypad 216 may operate to receive alphanumeric and control input information from a user/patient.

Vital signs portion 222 may operate to interface with vital sign monitoring devices and sensors. Non-limiting examples of devices and sensors interface via vital signs portion 222 include stethoscope 148 (FIG. 1), EKG equipment portion 150 (FIG. 1), blood pressure cuff 152 (FIG. 1), temperature monitor 156 (FIG. 1), oximeter 158 (FIG. 1), spirometer 160 (FIG. 1) and glucose monitor 162 (FIG. 1).

Video codec 224 may operate to code and decode video information.

Cabin management system 134 (FIGS. 1-2) may communicate bi-directionally with external communications and networking equipment via a communication channel 201, with video display 151 (FIGS. 1-2) via a communication channel 202 with video codec 224 via a communication channel 204, with video camera 145 (FIGS. 1-2) via a communication channel 206, second camera 164 (FIGS. 1-2) via a communication channel 208, with digital recorder 210 via a communication channel 212, with card terminal 124 via a communication channel 218, with keypad 216 via a communication channel 220 and with data concentrator 214 via a communication channel 223. Data concentrator 214 may communicate bi-directionally with vital signs portion 222 via a communication channel 226.

Cabin management system 134 (FIGS. 1-2) may operate as a central processor and communications hub for tele-health system 200. Cabin management system 134 (FIGS. 1-2) may operate to control the operation of and communication with video codec 224, video display 151 (FIGS. 1-2), video camera 145 (FIGS. 1-2), microphone 147 (FIGS. 1-2), audio portion 149 (FIGS. 1-2) and video display 151 (FIGS. 1-2) associated with video terminal 144 (FIG. 1).

Cabin management system 134 (FIGS. 1-2) may operate to control the operation of and communication with second camera 164 (FIGS. 1-2). Furthermore, cabin management system 134 may operate to control the operation of and communication with vital signs portion 222 for performing data acquisition via data concentrator 214.

Cabin management system 134 (FIGS. 1-2) may operate to control the operation of and communication with keypad 216 for receiving data input from user/patient.

Cabin management system 134 (FIGS. 1-2) may operate to control the operation of and communication with card terminal 124 (FIGS. 1-2) for reading customer information and storing information to a card device. Furthermore cabin management system 134 (FIGS. 1-2) may communicate information received from MCC 104 for storage to card device via card terminal 124 (FIGS. 1-2).

Cabin management system 134 (FIGS. 1-2) may operate to control the presentation out of instructional videos stored on digital recorder 210.

Cabin management system 134 (FIGS. 1-2) may operate to control the operation of and communication with video codec 224 for coding and decoding of video between video camera 145 (FIGS. 1-2), second camera 164 (FIGS. 1-2) and/or the satellite transceiver 108 (FIG. 1).

Figure 3A:
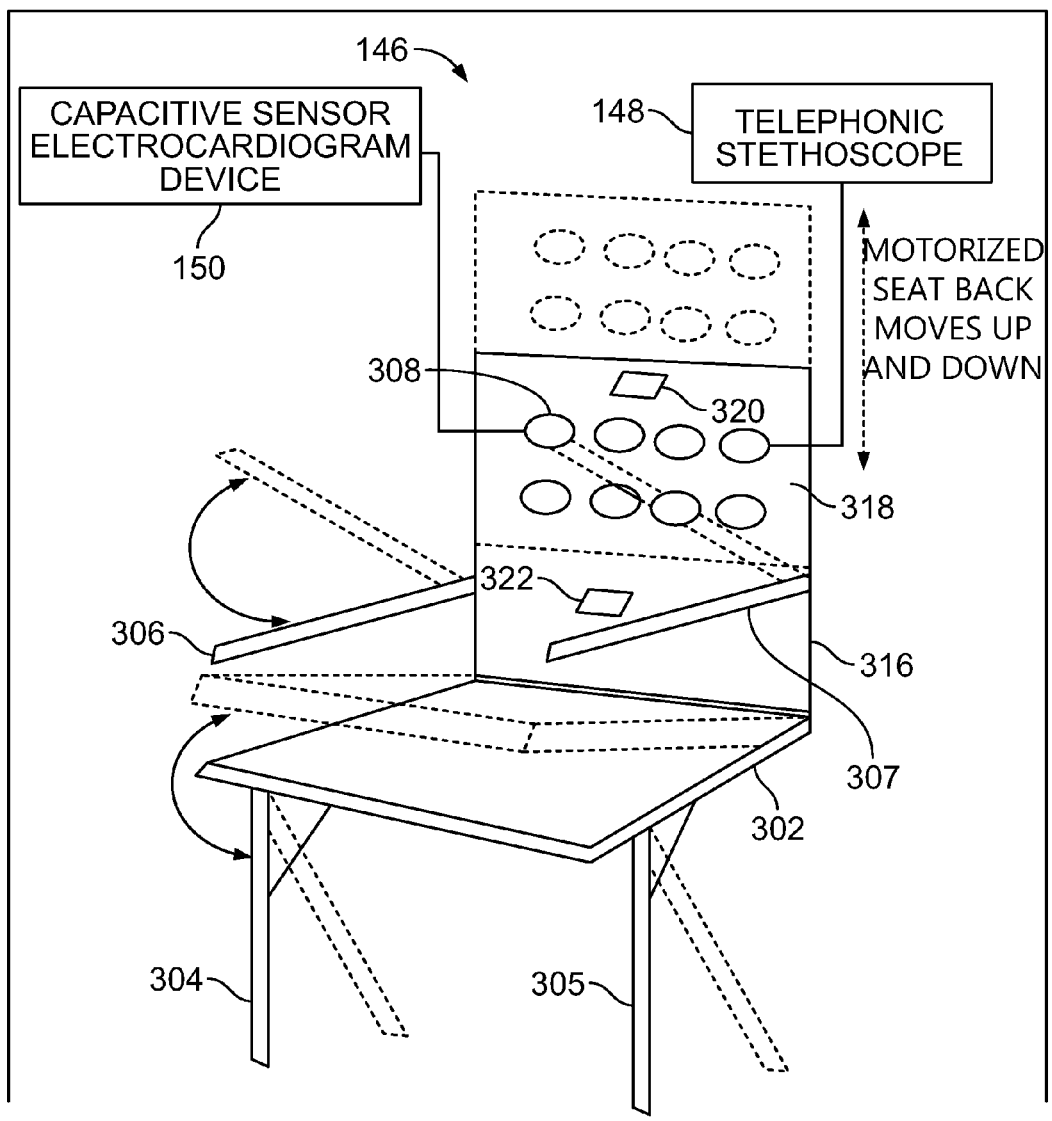
FIG. 3A is a perspective view illustrating a folding seat located in a tele-health cabin, according to an embodiment.

FIG. 3A is a perspective view illustrating a folding seat located in a tele-health cabin, in accordance with an embodiment.

Seat 146 (FIGS. 1, 3A) includes a folding leg 304, a folding leg 305, a folding arm 306, a folding arm 307, a multiplicity of sensors with a sampling denoted as a sensor 308, a multiplicity of audio sensors with a sampling denoted as an audio sensor 308, a back 316, a sitting portion 302, an electric motor 320, an electric motor 322, stethoscope 148 (FIGS. 1, 3A) and EKG equipment portion 150 (FIGS. 1, 3A).

Seat 146 (FIGS. 1, 3A) may operate to fold against the wall of tele-health cabin 106 (FIG. 1) when not in use. Furthermore, Seat 146 (FIGS. 1, 3A) may operate to fold against the wall of tele-health cabin 106 (FIG. 1) in order to permit space for wheelchair access.

Folding leg 304, folding leg 305, folding arm 306 and folding arm 307 may fold or collapse when operating folding seat 146 to fold against wall of tele-health cabin 106 (FIG. 1).

A multiplicity of sensors with a sampling denoted as sensor 308 may be located in back 316. Non-limiting examples for sensor 308 include capacitive sensors and audio sensors.

EKG equipment portion 150 (FIG. 1) may connect to sensors for measuring user/patient associated information. Non-limiting examples of measured information includes human heart functions. Furthermore, measurements recorded by sensor 308 may be performed through one layer of clothing.

A multiplicity of audio sensors with a sampling denoted as audio sensor 308 may be located in back 316. Audio sensors may be connected to stethoscope 148 (FIG. 1) for measuring the sound of blood traversing through a user/patient. Non-limiting examples of portions of a human body measured via audio sensors includes arteries, veins and heart. Audio sensors may operate to measure information through one layer of a user's/patient's clothing. Furthermore, information measured via audio sensors and stethoscope 148 (FIG. 1) may be communicated to MCC 104 (FIG. 1).

Back 316 may be configured via electric motor 320 and electric motor 322 and other mechanical devices in order to enable a medical practitioner with the capability to activate electric motors 320 and 322 and as a result transition seat back 316 up, down, left or right. Back 316 may be configured by medical practitioner such that sensors may contact with a user's/patient's back in an appropriate location.

Figure 3B:
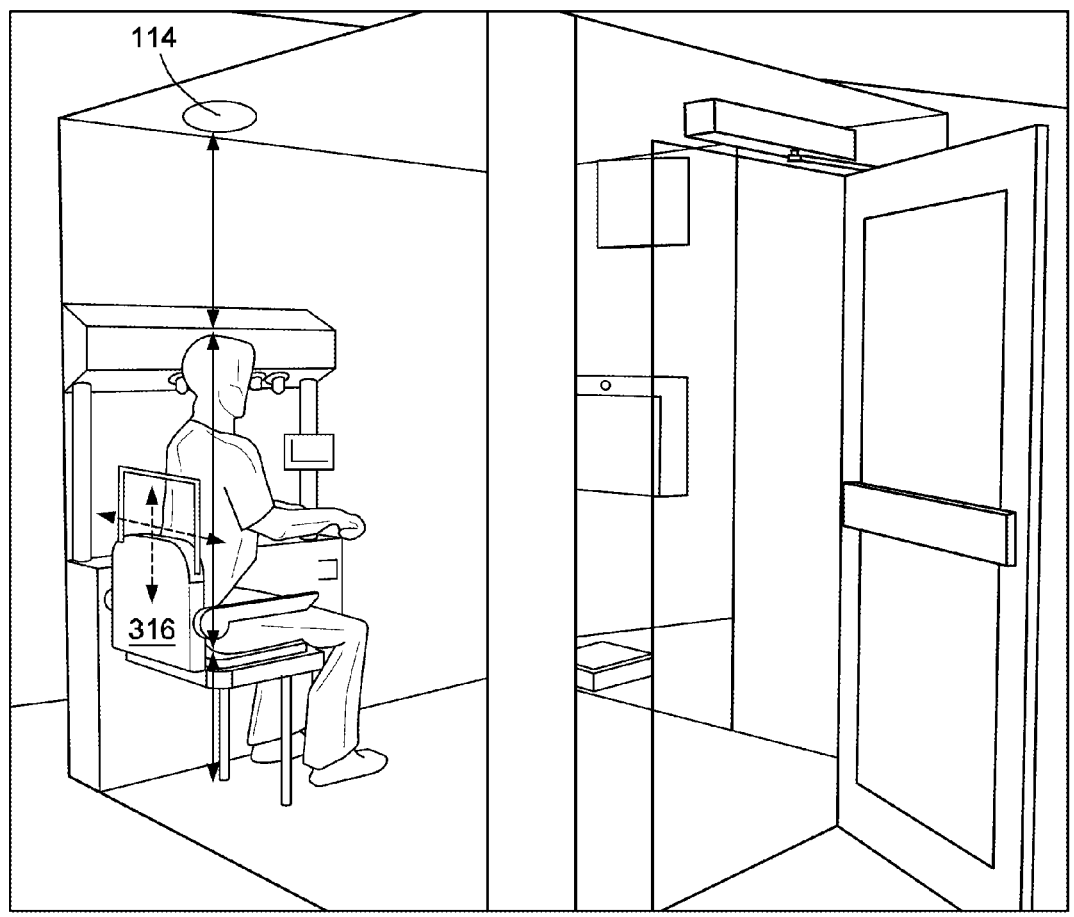
FIG. 3B is a perspective view illustrating the folding seat of FIG. 3A.

FIG. 3B is a perspective view illustrating the folding seat 146 of FIG. 3A. As discussed above with respect to FIG. 3A, audio sensors 308 are embedded in the back 316 of the seat 146. In an embodiment, audio sensors 308 may include a 4×4 array of 16 electronic stethoscope sensors embedded in the back 316 where a user/patient is seated for the virtual medical examination. The audio sensors 308 may be connected to stethoscope 148 for measuring the sound of blood traversing through a user/patient. The stethoscope array is mounted on a metal block (e.g., aluminum block) having corresponding mounting portions in the shape of an array (e.g., a "cupcake" type baking tray format), where the metal block shields the individual sensors from extraneous interference. A printed circuit board with 16 openings is positioned over the metal block such that that the 16 audio amplifiers located adjacent to each opening can be connected to the appropriate stethoscope sensor 308. Each of the 16 amplifiers is connected to a switch matrix which can be controlled remotely. At any given moment, only one stethoscope sensor is energized enabling it to pass audio signals from the user's/patient's lungs to a medical professional at the MCC 104. At the MCC 104, a representation of the user's/patient's body outline is presented on the screen of a computer terminal so the medical professional can select any one of the 16 sensors to be activated at a time.

An ultrasonic sensor 114 embedded in the ceiling of the tele-health cabin 106 is activated by the medical professional at the MCC 104 and measures the user's/patient's seated height when the user/patient first sits on the seat 146.

Data about the user/patient including age and gender is stored on a smart card which the user/patient inserts the smart card into a reader on entering the tele-health cabin 106. The user's/patient's age and gender data is used together with the user's/patient's seated height in the formula below to calculate the approximate location and size of the user's/patient's lungs.

In an embodiment, the collected data is used by the X-Y motorized seat back 316 to initially move or drive the array of stethoscope sensors 308 to appropriate points on the user's/patient's lungs. In other words, the X-Y motorized seat back 316 may automatically move the array of sensors 308 to an initial location based on the collected data.

In another embodiment, the medical professional at the remote MCC 104 can manually move the array of sensors 308 up or down and left or right for more precise alignment of the sensors 308 over the user's/patient's lungs.

The following formula is used to calculate the user's/patient's lung size and position and is used for the initial location the stethoscope array:

$$V=(B*R)+(B*Zv(S,A))$$

$$H=B*Zh(S,A)$$

In the above formulas, "V" is the vertical lung center of the user/patient, and "H" is the lung height of the user/patient. "B" is the seated height of user/patient, S is the gender of the user/patient, and R is the normal lung center location as a fraction of the seated height. Zv is table of vertical factors, and Zh is table of age and gender factors.

Accordingly, the vertical lung venter "V" is determined based on a combination of the normal lung center location "R" and a vertical factor based on the user's/patient's age and gender from the table "Zv." The lung height "H" is proportional to the user's/patient's height and a factor based on the user's/patient's age and gender from the table "Zh."

Figure 4:
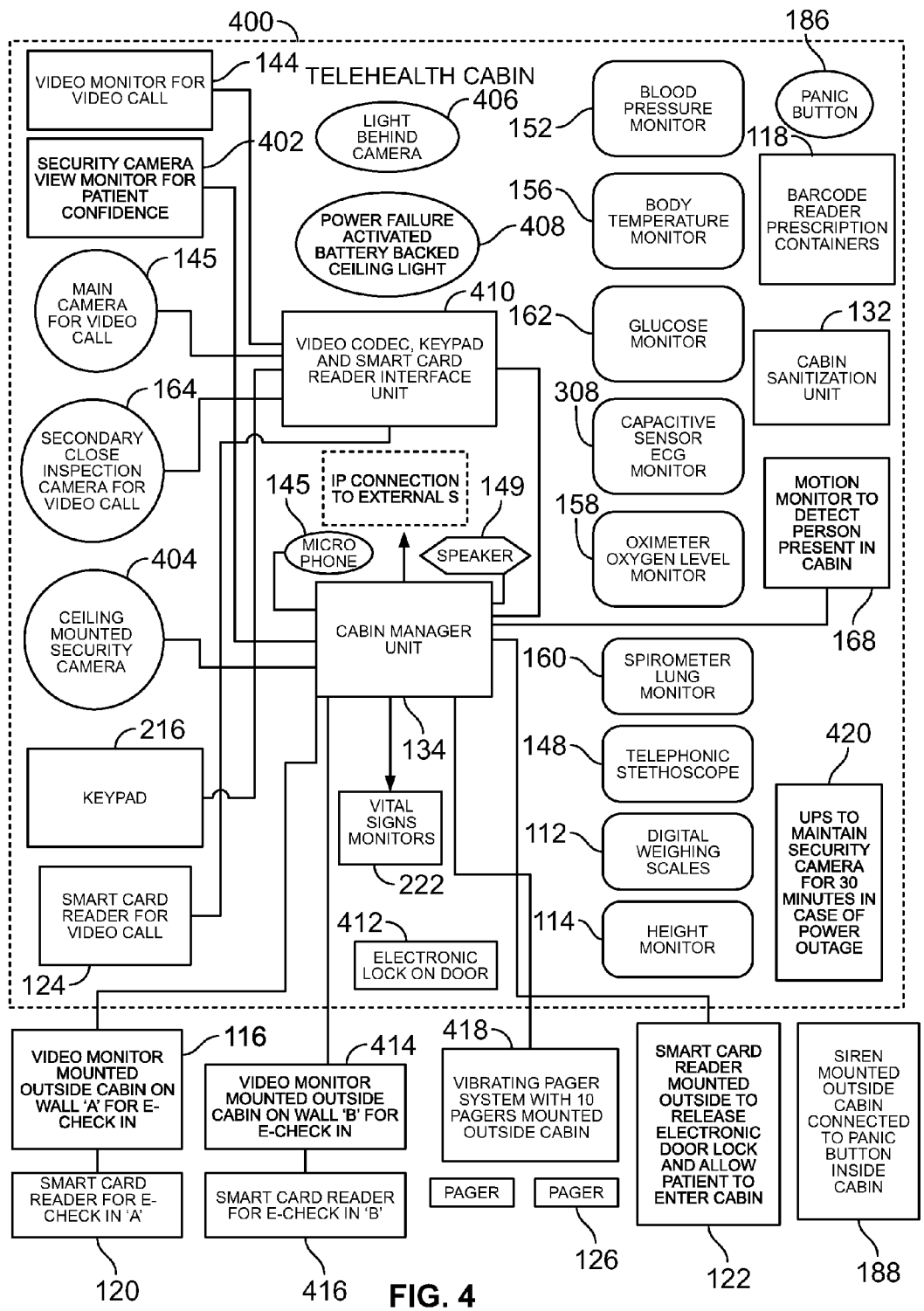
FIG. 4 is a diagram illustrating a system of components associated with the tele-health cabin shown in FIG. 1, according to an embodiment.

FIG. 4 is a diagram illustrating a system of components associated with tele-health cabin 106 of FIG. 1.

A system 400 includes video terminal 144 (FIGS. 1, 2, 4), a security camera monitor 402, video camera 145 (FIGS. 1, 2, 4), second camera 164 (FIGS. 1, 2, 4), a security camera 404, keypad 216 (FIG. 2), card terminal 124 (FIGS. 1, 4), terminal 116 (FIG. 1), card terminal 120 (FIG. 1), a light 406, a back-up light 408, an interface unit 410, microphone 147 (FIG. 1), audio portion 149 (FIG. 1), cabin management system 134 (FIG. 1), vital signs portion 222 (FIG. 2), a door lock 412, a terminal 414, a card terminal 416, a paging system 418, a multiplicity of vibrating page devices with a sampling denoted as vibrating page device 126 (FIG. 1), blood pressure cuff 152 (FIG. 1), temperature monitor 156 (FIG. 1), glucose monitor 162 (FIG. 1), sensor 308, oximeter 158 (FIG. 1), spirometer 160 (FIG. 1), stethoscope 148 (FIG. 1), digital scale 112 (FIG. 1), height measurement device 114 (FIG. 1), card reader 122 (FIG. 1), panic device 186 (FIG. 1), code scanner 118 (FIG. 1), sanitization device 132 (FIG. 1), presence detector 168 (FIG. 1), a backup power device 420 and siren 188 (FIG. 1).

Security camera monitor 402 may operate to present a view of the user/patient to the user/patient, so that if the user/patient attempts to damage the equipment or cabin structure then security personnel can be alerted and take appropriate action.

Security camera 404 may operate to capture and present a video representation of the internal view of tele-health cabin 106 to security camera monitor 402. Non-limiting examples for mounting or placement of security camera 404 include ceiling of tele-health cabin 106 (FIG. 1).

Light 406 may operate to provide lighting for internal area of tele-health cabin 106 (FIG. 1).

Back-up light 408 may operate to provide light illumination internal to tele-health cabin 106 (FIG. 1) in the event of a primary power failure.

Interface unit 410 may operate to provide control of and communications with various electronic equipment and sensors associated with tele-health cabin 106 (FIG. 1). Non-limiting examples of equipment include video codec, keypad and card terminals.

Door lock 412 may operate to provide a locking mechanism for tele-health cabin 106 (FIG. 1). Non-limiting examples for door lock 412 include electronic, electromechanical and automatic. Door lock 412 may be controlled via card reader devices and personal associated with MCC 104 (FIG. 1).

Terminal 414 may operate to provide similar features as described with reference to terminal 116 (FIG. 1).

Card terminal 416 may operate to provide similar features as described with reference to card terminal 120 (FIG. 1).

Paging system 418 may operate to provide notification information to users/patients.

Backup power device 420 may operate to provide power to tele-health cabin 106 (FIG. 1) in the event primary power fails to be provided.

Figure 5:
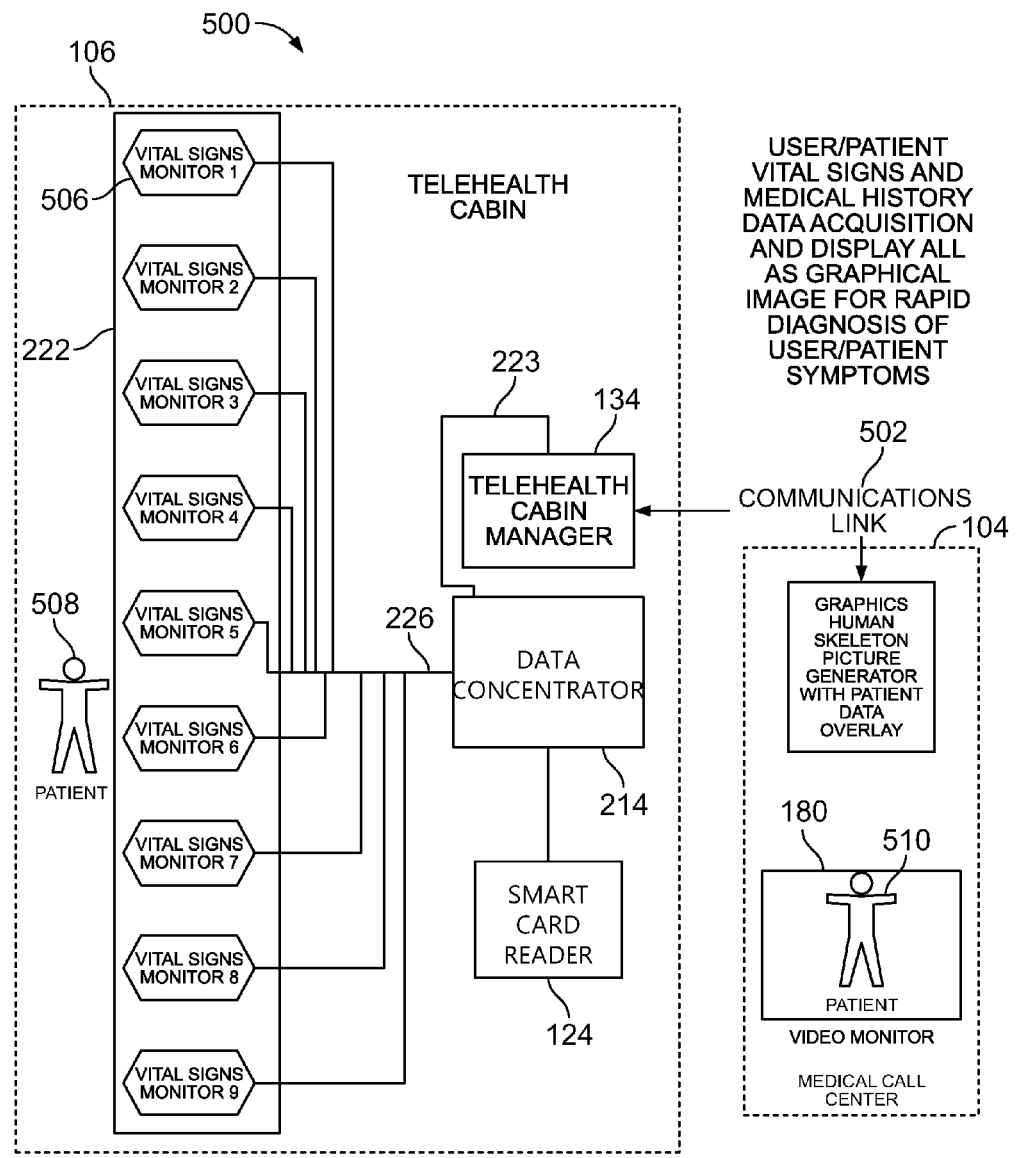
FIG. 5 is a diagram illustrating a tele-health system, according to an embodiment.

FIG. 5 is a diagram illustrating a tele-health system, according to an embodiment.

A tele-health system 500 includes tele-health cabin 106 (FIG. 1) and MCC 104 (FIG. 1).

Tele-health cabin 106 (FIG. 1) may communicate bi-directionally with MCC 104 (FIG. 1) via a communications channel 502. Non-limiting examples of communications channel 502 include satellite, cellular, wireless and terrestrial.

Tele-health cabin 106 (FIG. 1) includes cabin management system 134 (FIG. 1), data concentrator 214 (FIG. 2), card terminal 124 (FIG. 1) and vital signs portion 222 (FIG. 2).

Vital signs portion 222 (FIG. 2) includes a multiplicity of vital sign monitors with a sampling denoted as a vital sign monitor 506.

Vital sign monitor 506 may operate to measure and communicate vital sign information associated with a user/patient 508. Non-limiting examples of vital sign monitors include blood pressure, blood oxygen content, respiration, blood glucose and EKG.

Data concentrator 214 (FIG. 2) may operate to receive vital sign information from vital signs portion 222 (FIG. 2) and receive information associated with user/patient via card device presented to card terminal 124 (FIG. 1). Data concentrator 214 (FIG. 2) may process received information from vital sign monitor 506 and card terminal 124 (FIG. 1) and communicate processed information to cabin management system 134 (FIG. 1).

Cabin management system 134 (FIG. 1) may communicate information received from data concentrator 214 (FIG. 2) to MCC 104 (FIG. 1) via communications channel 502.

MCC 104 (FIG. 1) may operate to receive and process information from cabin management system 134 (FIGS. 1, 2) and present an information display 510 for viewing by a medical professional via remote terminal 180 (FIG. 1). Non-limiting examples of information display 510 include video, audio, text and images. Information display 510 may be processed and presented in a real-time manner such as to display an animated graphical profile of the user's/patient's body on avatar with layered overlays illustrating information associated with user/patient. Non-limiting examples of information presented include cardiac, digestive, respiratory and circulatory paths in such a manner as to allow the medical professional associated with MCC 104 to be able to make a diagnosis of the medical condition for user/patient 508. Furthermore, as a result of information display 510 received, medical professional may operate to further advance treatment of user/patient 508.

Figure 6:
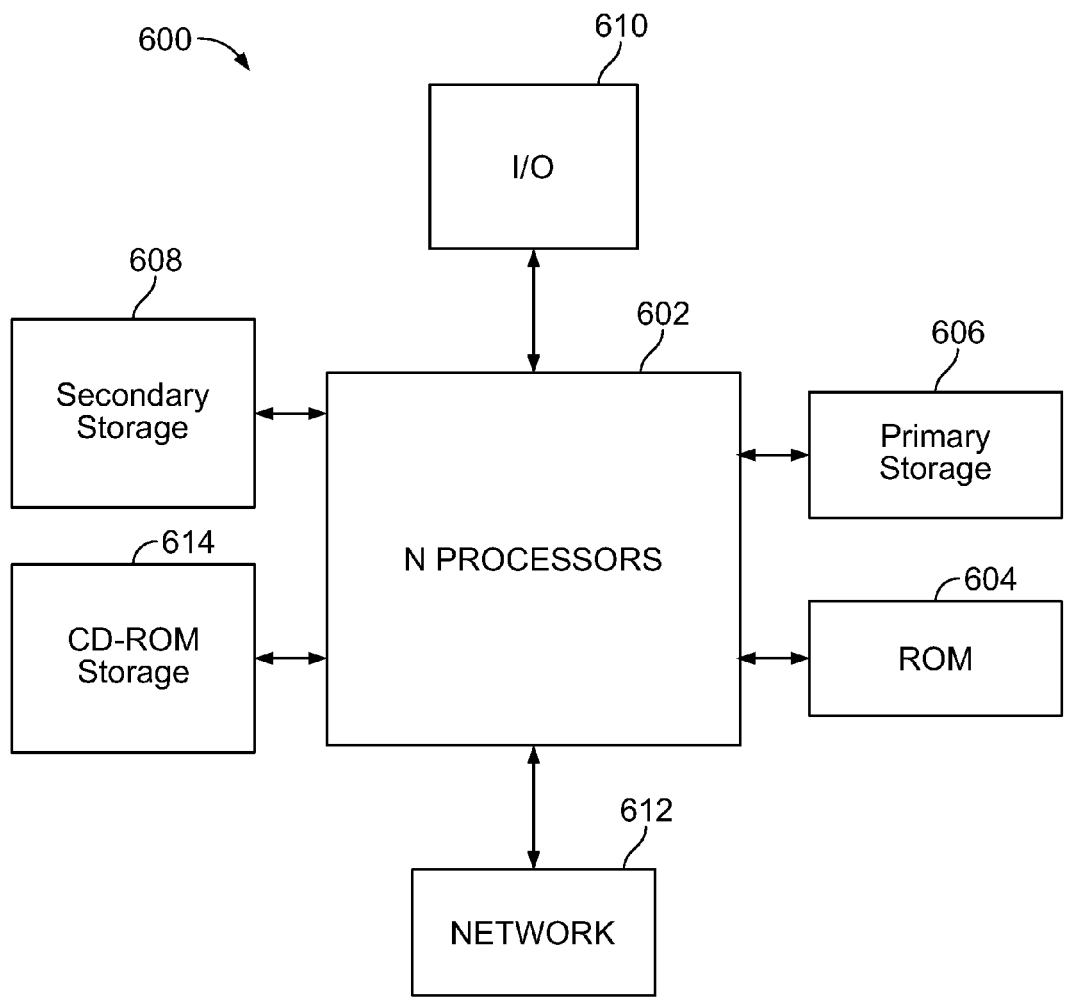
FIG. 6 is a diagram illustrating a computer system configured to be used in the tele-health system, according to an embodiment.

FIG. 6 is a diagram illustrating a computer system configured to be used in the tele-health system, according to an embodiment.

Computer system 600 includes a quantity of processors 602 (also referred to as central processing units, or CPUs) that may be coupled to storage devices including a primary storage 606 (typically a random access memory, or RAM), a primary storage 604 (typically a read only memory, or ROM). CPU 602 may be of various types including micro-controllers (e.g., with embedded RAM/ROM) and microprocessors such as programmable devices (e.g., RISC or SISC based, or CPLDs and FPGAs) and devices not capable of being programmed such as gate array ASICs (Application Specific Integrated Circuits) or general purpose microprocessors. As is well known in the art, primary storage 604 acts to transfer data and instructions unidirectionally to the CPU and primary storage 606 typically may be used to transfer data and instructions in a bi-directional manner. The primary storage devices discussed previously may include any suitable computer-readable media such as those described above. A mass storage device 608 may also be coupled bi-directionally to CPU 602 and provides additional data storage capacity and may include any of the computer-readable media described above. Mass storage device 608 may be used to store programs, data and the like and typically may be used as a secondary storage medium such as a hard disk. It will be appreciated that the information retained within mass storage device 608, may, in appropriate cases, be incorporated in standard fashion as part of primary storage 606 as virtual memory. A specific mass storage device such as a CD-ROM 614 may also pass data unidirectionally to the CPU.

CPU 602 may also be coupled to an interface 610 that connects to one or more input/output devices such as such as video monitors, track balls, mice, keyboards, microphones, touch-sensitive displays, transducer card readers, magnetic or paper tape readers, tablets, styluses, voice or handwriting recognizers, or other well-known input devices such as, of course, other computers. Finally, CPU 602 optionally may be coupled to an external device such as a database or a computer or telecommunications or internet network using an external connection shown generally as a network 612, which may be implemented as a hardwired or wireless communications link using suitable conventional technologies. With such a connection, the CPU might receive information from the network, or might output information to the network in the course of performing the method steps described in the teachings of the present disclosure.

FIGS. 7A-7D are flowcharts illustrating a method 700 of operating a tele-health system, according to an embodiment.

Figure 7A:
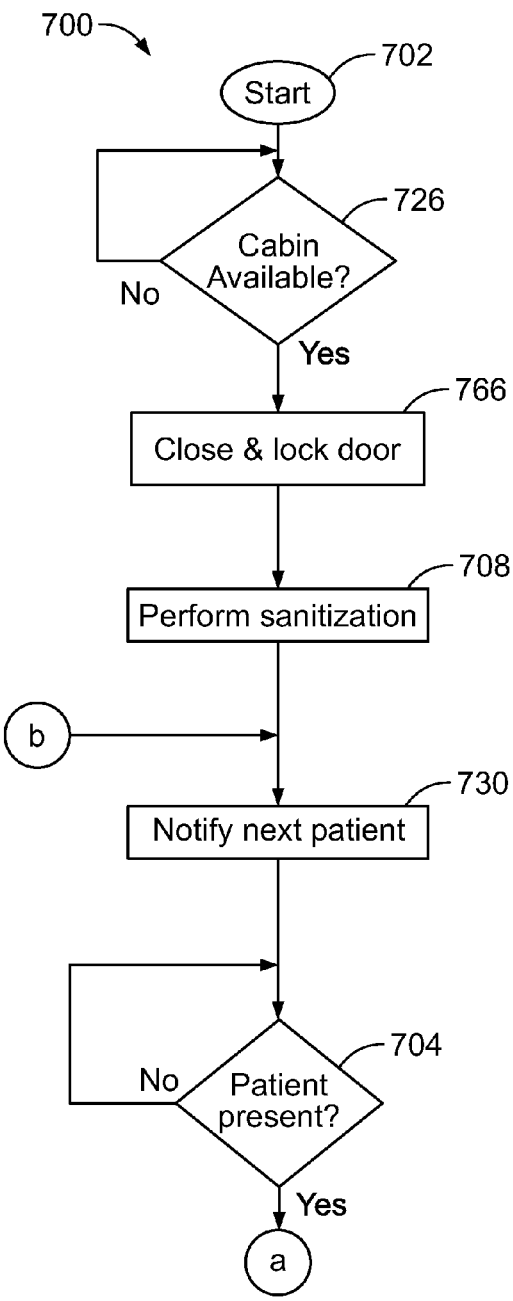
FIGS. 7A-7D are flowcharts illustrating a method of operating a tele-health system, according to an embodiment.
Figure 7B:
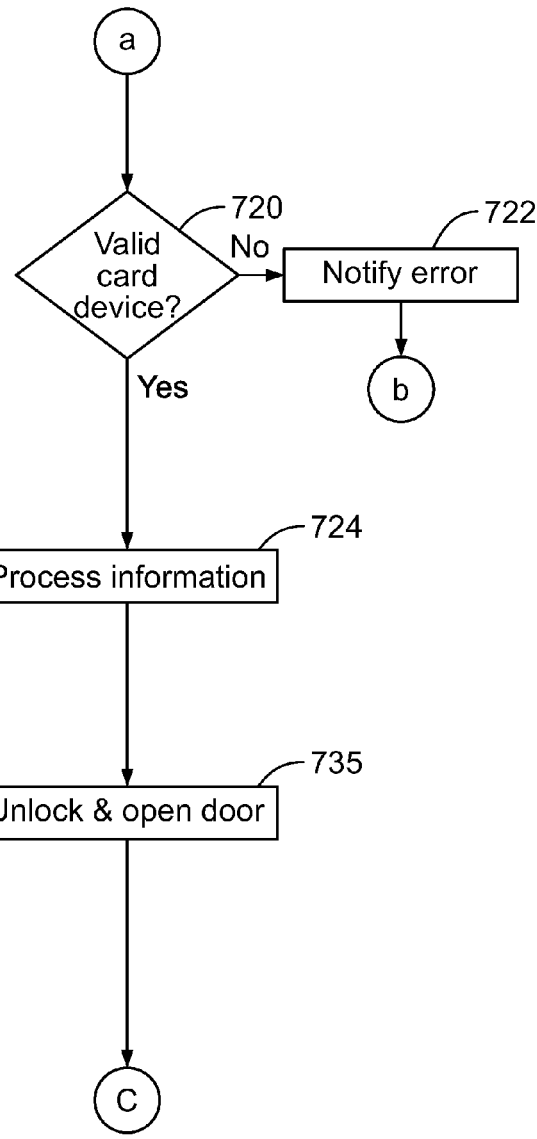
Figure 7C:
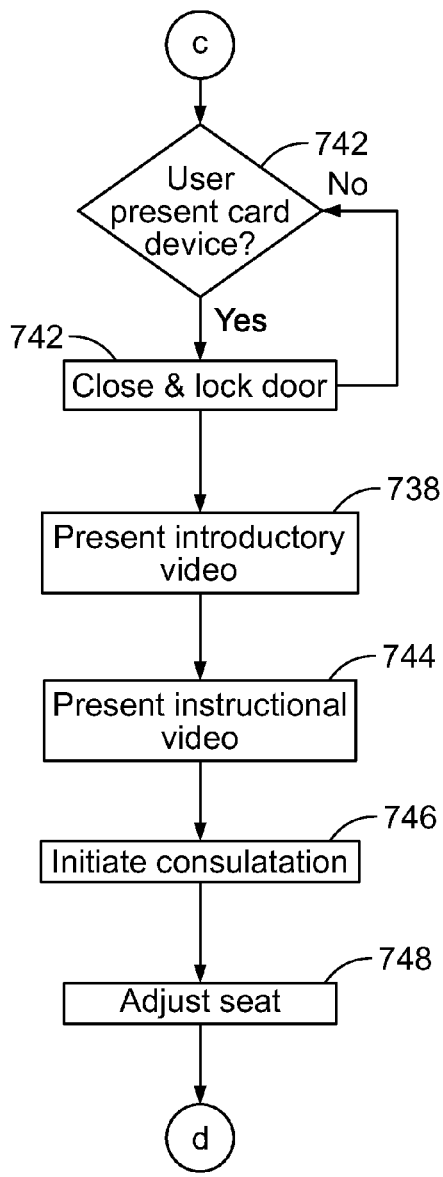
Figure 7D:
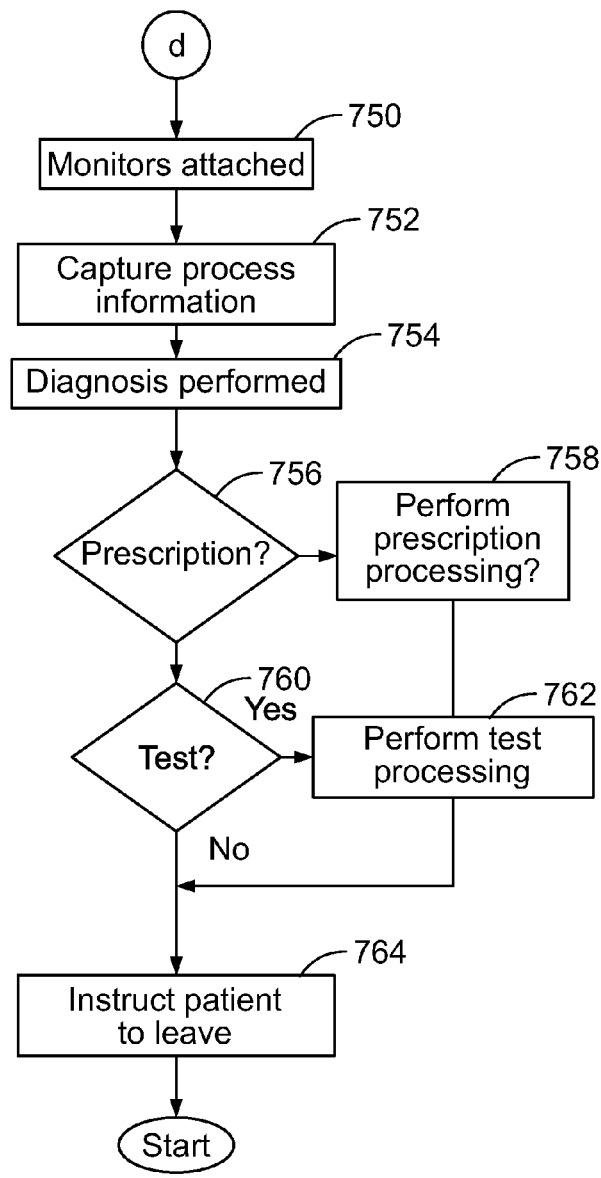

For method 700, the process initiates at step 702 (FIG. 7A).

A determination of an available tele-health cabin 106 (FIG. 1) may be performed at step 726.

At step 766, the door 128 (FIG. 1) may be closed and locked via door lock 412 (FIG. 4). Following closing and locking door at step 766, execution of method 700 transitions to step 708.

Sanitization is performed at step 708. To perform sanitization, cabin management system 134 (FIG. 1), after detecting unsanitary condition, may configure sanitization device 132 (FIG. 1) to perform sanitization of tele-health cabin 106 (FIG. 1).

The next available user/patient may be notified via paging system 418 (FIG. 4) and vibrating page device 126 (FIG. 1) at step 730.

The systems will wait for a predetermined time for the next patient and a determination of no user present at step 704 after which the next available patient will notified as in the previous step.

At step 720 (FIG. 7B), a determination for a valid card device may be performed. For a determination of an invalid card device at step 720, user may be notified of an error at step 722 followed by transition of method 700 to step 730 (FIG. 7A).

For a determination of a valid card device at step 720, information presented via card device and via user/patient input may be processed at step 724.

For a determination of a valid card device at step 732, door 128 (FIG. 1) may be unlocked via door lock 412 (FIG. 4) and automatically opened at step 735.

For a determination of the presence of a user/patient, at step 738, door 128 (FIG. 1) may be closed and locked via door lock 412 (FIG. 4).

At step 740, user/patient may be presented an introductory video via video terminal 144 (FIG. 1).

At step 742, a determination may be performed to determine if user/patient has presented card device to card terminal 124 (FIG. 1). For a determination of a user/patient presenting card device to card terminal 124 (FIG. 1) in step 742, an instructional video may be presented to user/patient via video terminal 144 (FIG. 1) in a step 744.

At step 746, a consultation may be initiated between user/patient located in tele-health cabin 106 (FIG. 1) and medical professional associated with MCC 104 (FIG. 1).

At step 748, seat 146 (FIG. 1) may be adjusted in order to obtain proper orientation of sensors associated with back 316 (FIG. 3) of seat 146 (FIG. 1).

In a step 750 (FIG. 7D), monitoring devices and sensors may be attached to user/patient by user/patient.

At step 752, information associated with user/patient may be captured, communicated and processed by tele-health cabin 106 (FIG. 1). Furthermore, information may be communicated to remote terminal 180 (FIG. 1) of MCC 104 (FIG. 1) for use by medical professional for determining a diagnosis or determining further steps for treatment.

At step 754, medical professional associated with MCC 104 (FIG. 1) may perform a diagnosis of user/patient.

At step 756, a determination of generating a prescription may be performed. For a determination of generating a prescription in step 756, at step 758 a prescription may be generated. Non-limiting examples of efforts performed for generating a prescription include transmitting prescription information to a pharmacy and/or to user's/patient's card device.

At step 760, a determination of generating a medical test may be performed. For a determination of generating a medical test in step 760, at step 762 a medical test may be created. Non-limiting examples of efforts performed for generating a test include transmitting test request to medical test facility and/or to user's/patient's card device.

At step 764, a determination of the presence of a user/patient may be performed. For a determination of a lack of presence for a user/patient at step 764.

<Hands-Free Remote Controlled Medical Device and a Medical Device Station>

In another embodiment, a medical device station enables a medical device to be used by a plurality of users in a public access location including an unmanned micro clinic (e.g., the tele-health cabin 106) without cleaning the medical device after each usage. The medical device station includes an enclosure having an opening formed therein, and a medical device housed in the enclosure, where a test strip receptacle of the medical device is aligned with the opening form in the enclosure. This medical device station shields the medical device from user contact and permits only the user test strip to be inserted through the opening of the enclosure surrounding the device.

The enclosure may be made of a rigid material with a small opening cut into one side of the enclosure. The opening allows a single use test strip to be inserted into the receptacle of the medical device mounted inside the enclosure without the user's hand making contact with the medical device, thereby eliminating the requirement to clean the medical device after each usage.

The medical device may be mounted on a bracket in a horizontal plane inside the enclosure with the opening permitting ingress into the medical device of a test strip. The medical device may be retracted so that the test strip is clear of the opening. The medical device may be rotated about 90 degrees to the vertical plane with the receptacle containing the test strip to be positioned at the bottom of the medical device.

In an embodiment, the medical device may be mounted on a movable arm of the bracket. The movable arm may be controlled remotely by a computer in the micro clinic or by a computer in a remote hospital medical call center. In another embodiment, the movable arm may be programmed to automatically retract or extend after a predetermined period of time has elapsed.

The medical device may eject the test strip into a receptacle or waste bin positioned below the medical device inside the enclosure.

The medical device may be rotated back to the horizontal plane and extended to be in close proximity to the enclosure wall with the test strip receptacle aligned with the opening in the enclosure wall making the medical device ready for use by the next user.

The medical station may further include a communications device which enables the medical device to transmit the results of the medical tests carried out on the test strip to be sent to a computer through a first communications link. The computer may transmit the test results through a second communications link to a computer at a hospital medical call center. In another embodiment, the communication device may transmit the results of the medical tests directly to the computer at the hospital medical call center.

In various embodiments, the medical device may include a blood glucose monitor or a cholesterol monitor.

FIGS. 8A-8E are diagrams illustrating a medical device station 800 including a blood glucose monitor 810, according to an embodiment.

Figure 8A:
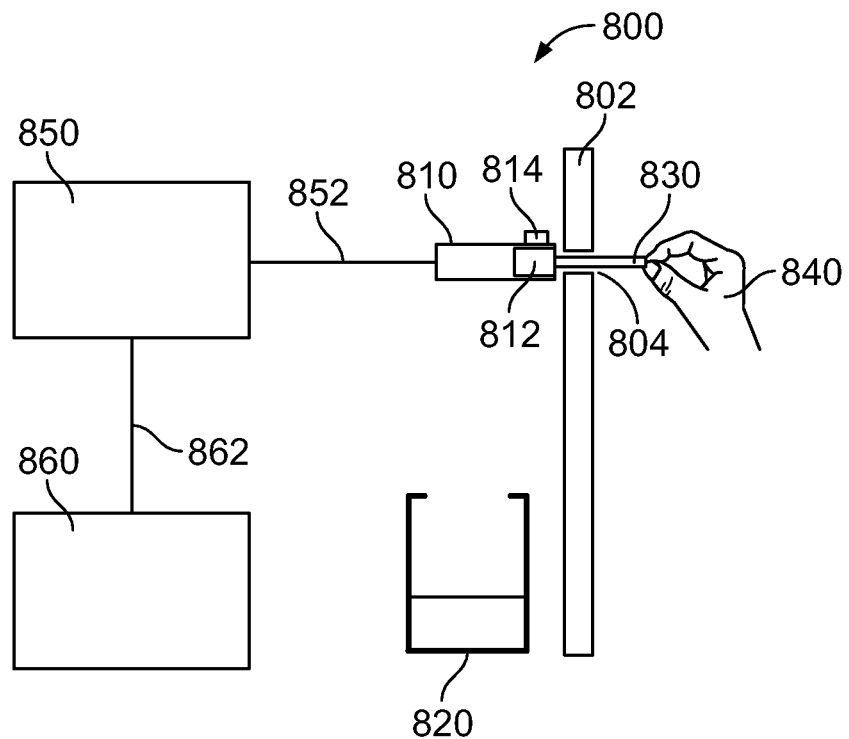
FIGS. 8A-8E are diagrams illustrating a medical device station including a blood glucose monitor, according to an embodiment.
Figure 8B:
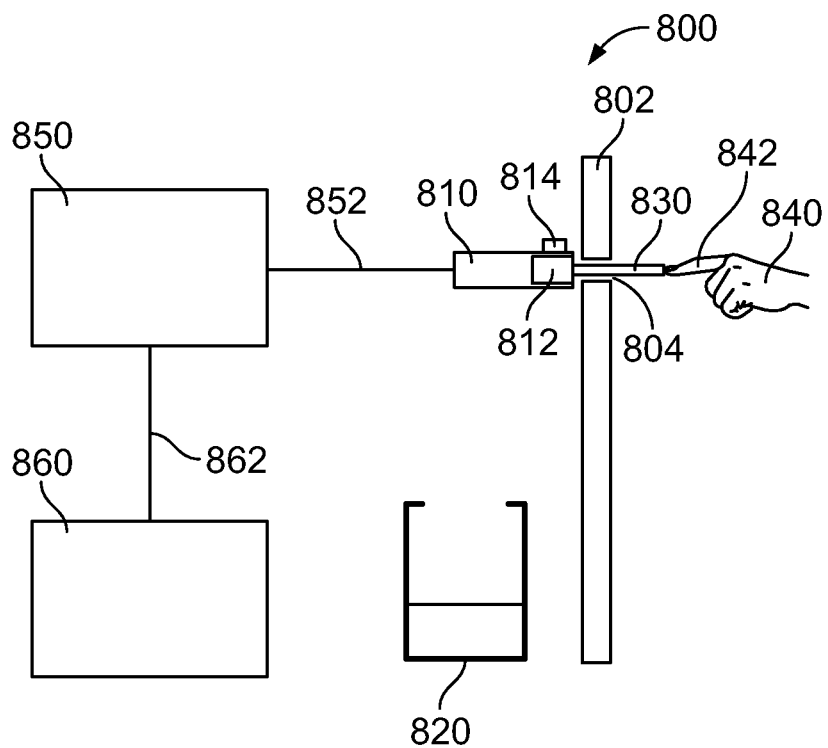

In FIGS. 8A and 8B, the medical device station 800 includes an enclosure 802 having an opening 804 formed thereon, and a medical device 810 housed in the enclosure 802, where a test strip receptacle 812 of the medical device 810 is aligned with the opening 804 formed in the enclosure 802. The opening 804 may be a slot or opening of other shapes based on a test strip receptacle 812 of the medical device 810. The medical device station 800 may be located and used in an unmanned micro clinic, such as the tele-health cabin 106 of FIG. 1. In the present embodiment, the medical device 810 is a blood glucose monitor 810. In another embodiment, the medical device may be a cholesterol monitor.

A user wishing to check his or her blood glucose level in the tele-health cabin 106 or similar location purchases a single use medical lance and a single use blood glucose monitor test strip 830 from a dispensing station. The dispensing station may be located inside or outside the tele-health cabin 106.

The user enters the tele-health cabin 106 or similar location, and when directed by a remotely located medical professional at the MCC 104, the user then inserts the test strip 830 through the opening 804 in the enclosure 802, which contains the blood glucose monitor 810. The blood glucose monitor 810 includes a test strip receptacle 812 designed to accept the test strip 830, and the test strip receptacle 812 is aligned with the opening 804 in the enclosure 802. The enclosure 802 may be sealed except for the opening 804. The enclosure may be mounted on a wall of the tele-health cabin 106 or may be free standing in the tele-health cabin 106.

The user lances a finger to produce a small amount of blood and applies the blood to the exposed part of the test strip 830, which protrudes from the opening 804 in the enclosure 802. Because the blood glucose monitor 810 is housed completely within the enclosure 802, the enclosure 820 protects the blood glucose monitor 810 from being touched by the user's hand 840.

The medical professional located at the remote MCC 104 is able to see the user action via a two-way video system (a first video system installed in the tele-health cabin 106 and a second video system installed in the remote MCC 104). Once the user has placed blood on the test strip 830, the medical professional enters a command on a computer 860 located at the remote MCC 104 which uses a second communications link 862 to send a command to a computer 850 located in the tele-health cabin 106. The computer 850 then relays the command via a first communications link 852 to the blood glucose monitor 810. In another embodiment, the user may send a command directly to the blood glucose monitor 810 via the computer 850 located in the tele-health cabin 106.

The command sent to the blood glucose monitor 810 instructs the blood glucose monitor 810 to relay the blood glucose test results through the first communications link 852 to the computer 850 in the tele-health cabin 106 for relay through the second communications link 862 to the computer 860 at the MCC 104. At the MCC 104, the test results are displayed on a computer screen for the medical professional to evaluate. Additionally, the results may also be stored on digital media in the computer 860 at the MCC 104 or on another networked computer. In another embodiment, the blood glucose test results may be sent directly to the computer 860 at the remote MCC 104, bypassing the computer 850 in the tele-health cabin 106.

Figure 8C:
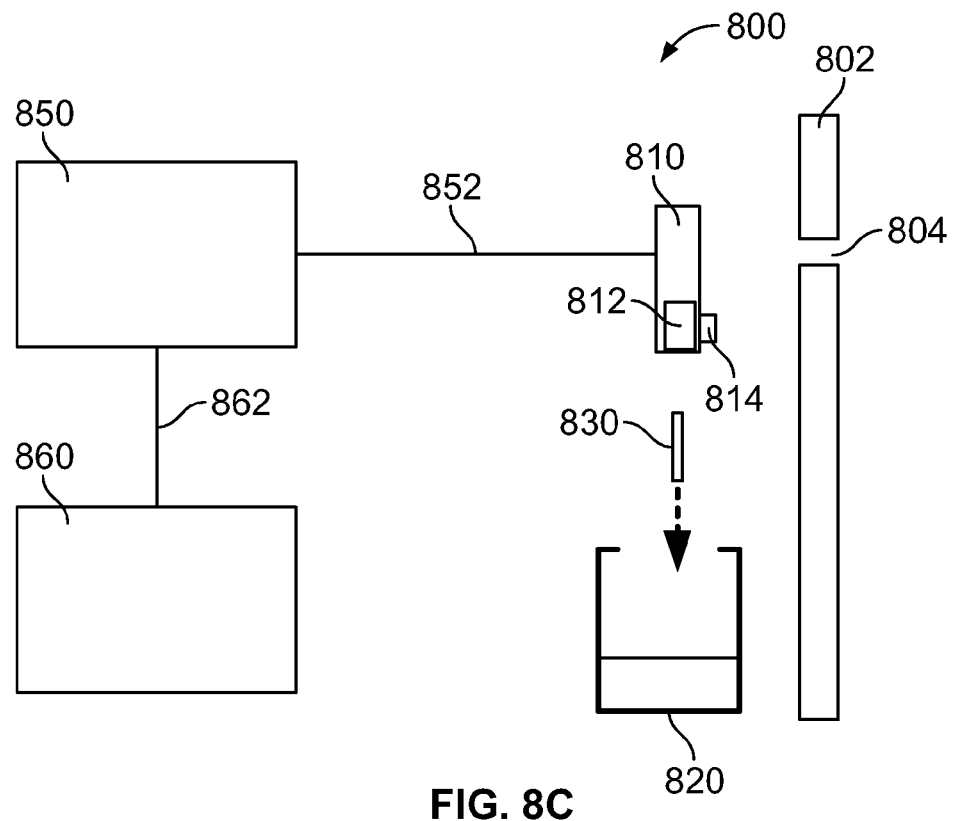
Figure 8D:
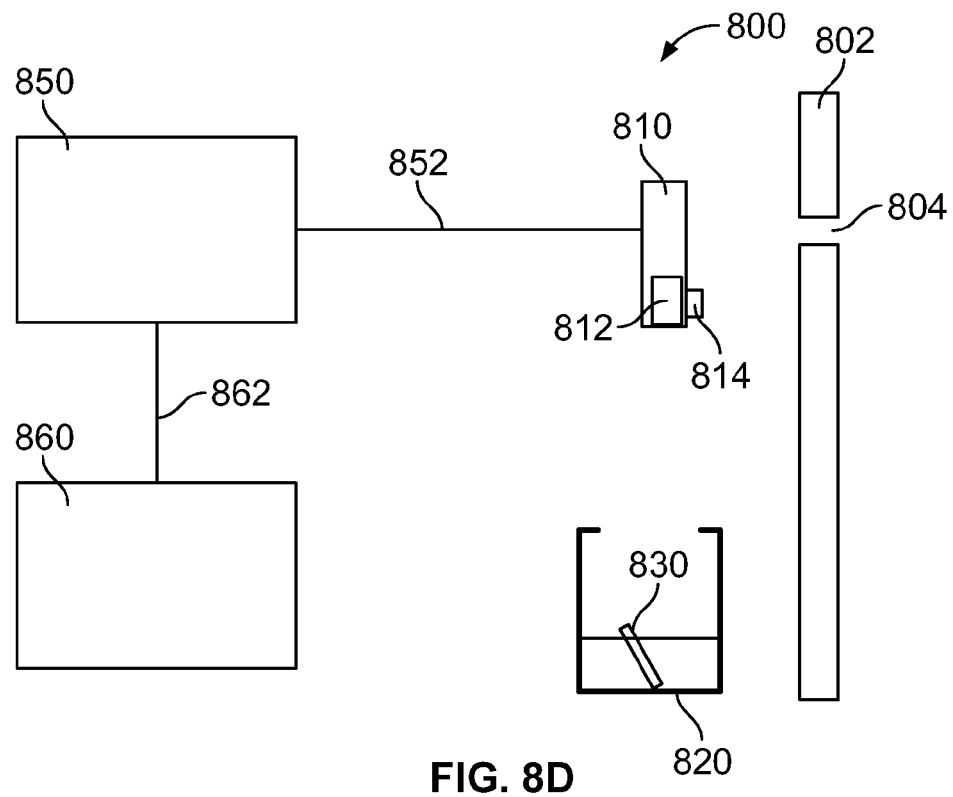

FIGS. 8C and 8D are diagrams illustrating the blood glucose monitor 810 being rotated to retract and ejecting a user test strip 830, according to an embodiment. The blood glucose monitor 810 may be mounted on a bracket (not shown) in a horizontal plane inside the enclosure 802. The bracket may include a first movable arm on which the blood glucose monitor 810 is mounted. The first movable arm may be controlled by the computer 850 in the tele-health cabin 106 or by the computer 860 in the remote MCC 104. If the blood glucose monitor 810 includes a test strip eject button or key 814, the bracket may further include a second movable arm controllable to push the test strip eject button 814. Like the first movable arm, the second movable arm may be controlled by the computer 850 in the tele-health cabin or by the computer 860 in the remote MCC 104.

In the present embodiment, when the user examination is complete, the medical professional issues a command on the computer 860 at the MCC 104 which is transmitted through the second communications link 862 to the computer 850 in the tele-health cabin 106. The computer 850 in the tele-health cabin 106 relays the control signal through the first communications link 852 to the blood glucose monitor 810. In another embodiment, when the examination is complete, the user may issue a command to the blood glucose monitor 810 using the computer 850 in the tele-health cabin 106. In yet another embodiment, after a predetermined period of time has elapsed after the examination is complete (e.g., about 30 seconds or about 60 seconds), the computer 850 in the tele-health cabin 106 may automatically issue a command to the blood glucose monitor 810.

When a retract command signal is received at the blood glucose monitor 810, the retract command causes the first movable arm to retract the blood glucose monitor 810 away from a wall of enclosure 802 at a sufficient distance so that the test strip is clear of the opening 804 in the enclosure wall 802. The first movable arm then rotates the blood glucose monitor about 90 degrees from the horizontal plane to the vertical plane. In an embodiment, an issued eject command causes the second movable arm to press the eject button 814 to eject the used test strip 830 safely into a waste bin 820 located below the blood glucose monitor 810 inside the enclosure 802.

In other embodiments, if the blood glucose monitor 810 does not include a test strip eject button or key, the first movable arm may automatically retract and rotate the blood glucose monitor 810 after a predetermined time has elapsed to dispose the used test strip 830 in the waste bin 820 below the blood glucose monitor 810. In another embodiment, the blood glucose monitor 810 is not retracted or rotated after the examination, but instead, the blood glucose monitor 810 may eject the used test strip 830 through the opening 804 formed in the enclosure 802 so that the user may dispose the used test strip 830.

Figure 8E:
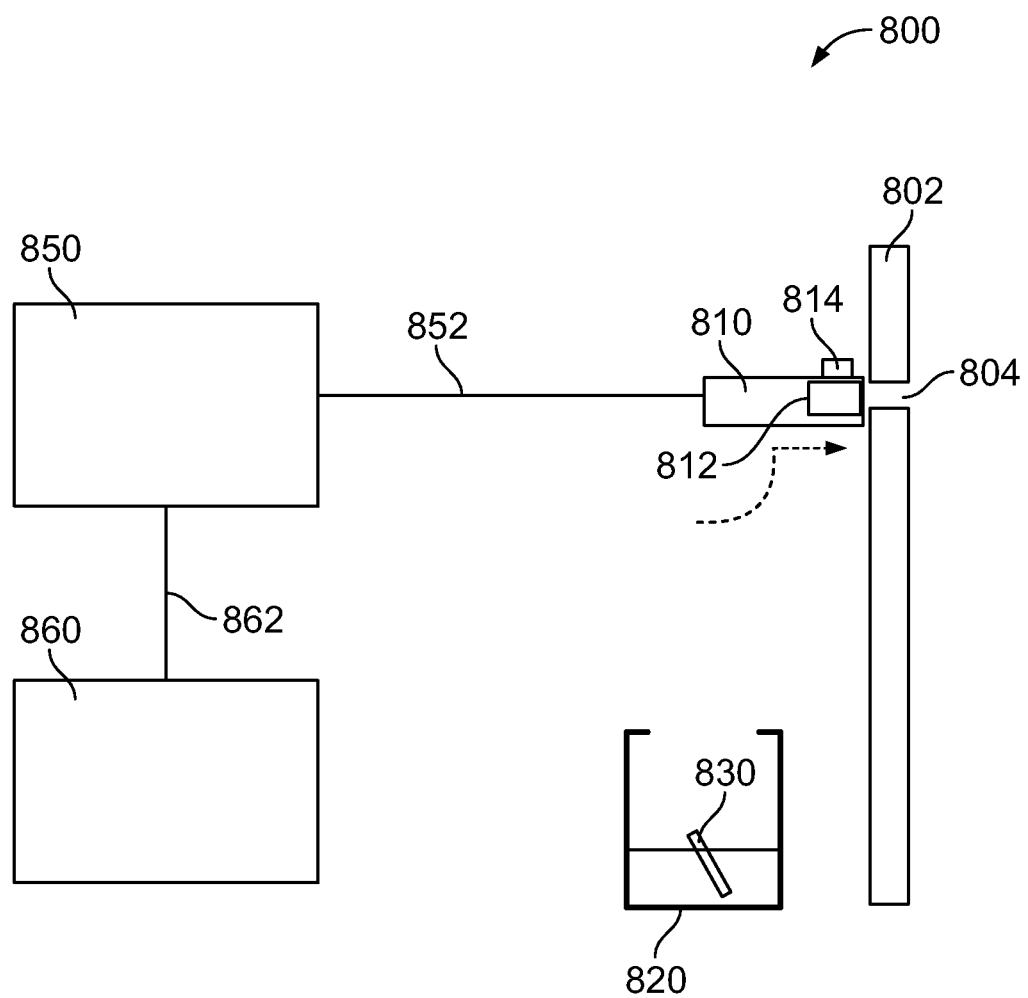

FIG. 8E is diagram illustrating the blood glucose monitor 810 being rotated to its original position, according to an embodiment.

When the used test strip 830 has been ejected, the first movable arm rotates the blood glucose monitor 810 about 90 degrees back to the horizontal plane. The first movable arm then extend the blood glucose monitor 810 toward the enclosure wall 802 so that the blood glucose monitor 810 is in close proximity to the enclosure wall 802 with the test strip receptacle 812 aligned with the opening 804 in the enclosure wall 802. Once the blood glucose monitor 810 has returned to its original position, it is ready for use by the next user.

<Automatic Cleaning System for a Tele-Health Cabin>

An automatic cleaning system is used for the automated dispensing, retraction and cleaning of a single medical instrument. These functions may be locally or remotely initiated if the automatic cleaning system is implemented in the tele-health cabin 106 or similar location.

Figure 9:
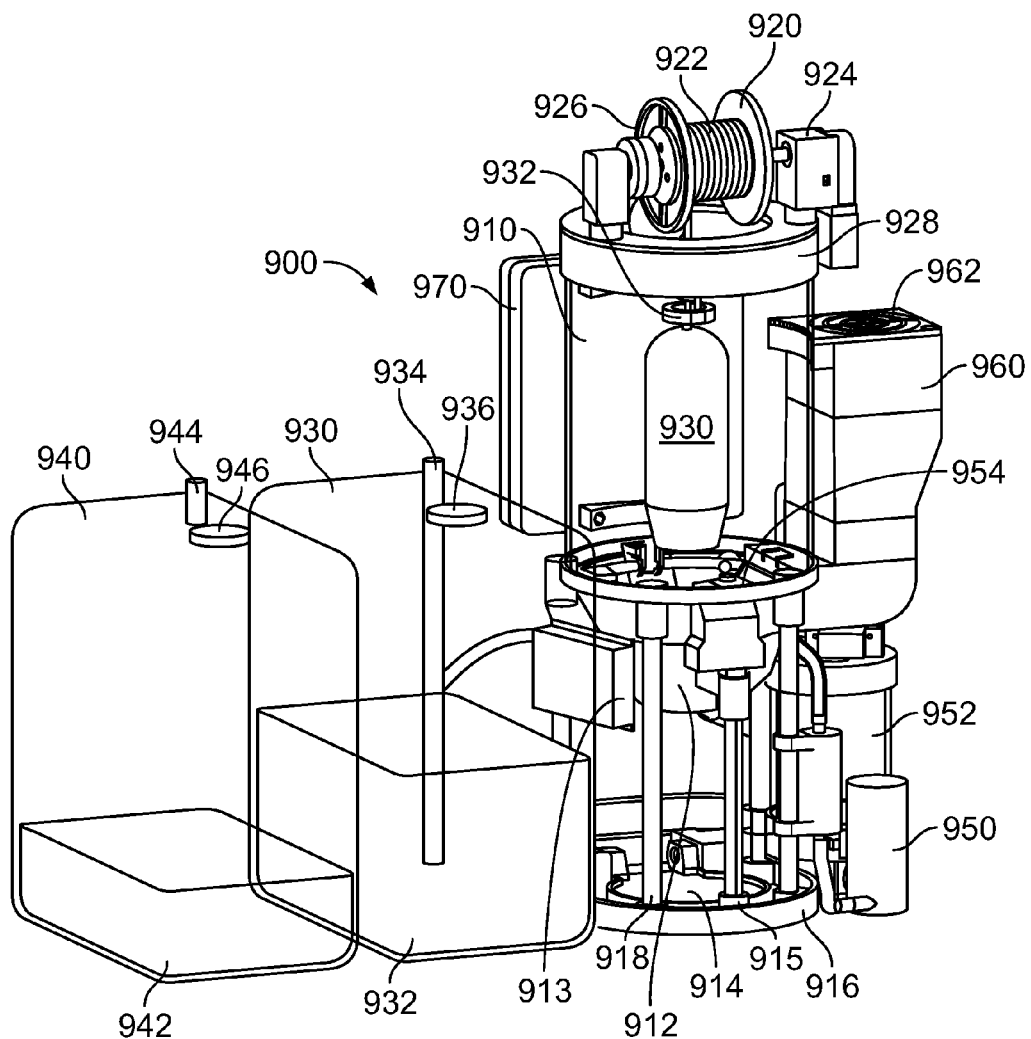
FIG. 9 is a perspective view of an automatic cleaning system for a tele-health cabin, according to an embodiment.
Figure 10D:
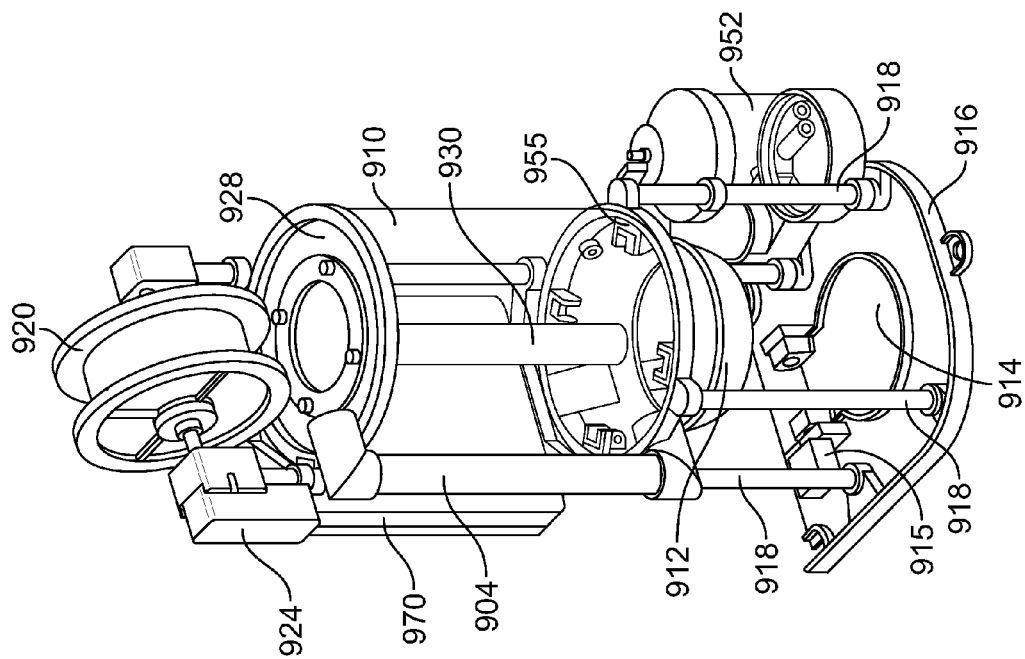
Figure 10C:
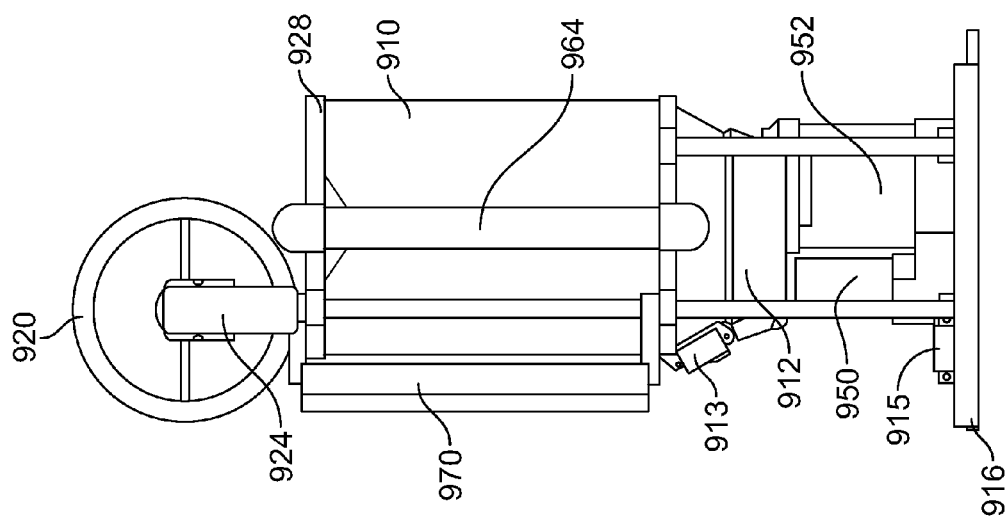

FIG. 9 is a perspective view of an automatic cleaning system 900 for a tele-health cabin 106, according to an embodiment. FIG. 10A is a front perspective view of a cleaning device of the automatic cleaning system 900, FIG. 10B is a back perspective view of the cleaning device, FIG. 10C is a side view of the cleaning device, and FIG. 10D is a perspective view of the cleaning device.

As shown in FIG. 9, the automatic cleaning system 900 includes the cleaning device, a primary reservoir 930 and a waste fluid reservoir 940. The cleaning device includes a cleaning chamber 910, which is a receptacle for a medical instrument 930 to be cleaned after use by a user. The medical instrument 930 is suspended within the cleaning chamber 910 by a cable 922, which also provides power and data communications to the medical instrument 930. A motorized locking mechanism and two motorized flaps (912, 914) are disposed at the bottom of the cleaning chamber 910 to open and close the cleaning chamber 910 and to permit the medical instrument 930 to exit the lower opening of cleaning device. The motorized flap includes an upper flap 912 and a lower flap 914. The upper flap 912 may be cup-shaped and may be provided to close the bottom of the cleaning chamber 910. The lower flap 914 may be flat and may be provided to prevent user access during the cleaning process.

In the embodiment shown in FIG. 9, the primary reservoir 930 and the waste fluid reservoir 940 are disposed alongside the cleaning chamber 910. In another embodiment, the primary reservoir 930 and the waste fluid reservoir 940 are positioned below the cleaning chamber 910 to prevent syphoning of the cleaning solution from the primary reservoir 930 and to allow gravity draining of the waste solution to the waste fluid reservoir 940.

In an embodiment, the cleaning chamber 910 may include a fixed vertical cylinder of a sufficient dimension to fully accommodate the medical instrument 930 to be decontaminated completely within the cleaning chamber 910. The cleaning chamber 910 may further include a lid 928 disposed on top of the vertical cylinder for sealing the interior of the cylinder. A small centrally located access aperture is formed in the lid 928 to provide passage for the cable 922, which carries power and/or communications to the medical instrument 930.

A motor pulley mechanism (e.g., winch) is disposed above the lid 928 and is used to dispense the medical instrument 930. The motor pulley mechanism includes a cable spool 920 (or pulley), the cable 922, a motor 924, and a drag clutch 926.

The motor pulley mechanism delivers the medical instrument 930 to within an arm's reach of the user. The motor pulley mechanism is disposed above the lid 928 to move the medical instrument 930 in and out of the cleaning chamber 910. A sensor 932 may be mounted on the lid 928 in the interior of the vertical cylinder to detect when the medical instrument 930 has reached its top limit of travel inside the vertical cylinder (i.e., the sensor 932 detects when the medical instrument 930 is at the top of the cleaning chamber 910). The cable 922 may be routed over the top of the cleaning chamber 910 by a driven pulley and then looped over idler pulleys and counter weight to form a "U"-shaped loop of cable in a cable shaft. One end of the cable 922 may be connected to external power and communications.

A cup-shaped flap 912 (or bowl-shaped flap) is hingedly connected with an opening/closing actuator 913 to the bottom of the vertical cylinder of the cleaning chamber 910. The cup-shaped flap 912 selectively closes and seals the interior of the cylinder in a closed configuration or allows and provides access to the cylinder interior in an open configuration. The cup-shaped flap 912 is hingedly connected to the vertical cylinder portion of the cleaning chamber 910 to collect decontamination fluids. A waste pipe is coupled to the cup-shaped flap 912 to return the collected decontamination fluids to a secondary wash cycle reservoir 952.

A base plate or drip plate 916 is disposed below the cleaning chamber 910 and the cup-shaped flap 912. The drip plate 916 is coupled to and separate from the cleaning chamber 910 via supports 918. An entrance flap 914 with an opening/closing actuator 915 is coupled to the drip plate 916 and is disposed below the cup-shaped flap 912 for selectively closing access to the area under the cup-shaped flap 912 to prevent user access to the cleaning chamber 910. The entrance flap 914 closes over a raised base plate lip formed around part of the perimeter of the entrance flap 914. The raised base plate lip forms a channel around the entrance flap 914 to collect and drain away from the area any drips of fluid which may fall from the cup-shaped flap 912. When the entrance flap 914 is opened, the user is provided access to the area below the cup-shaped flap 912 and above the drip plate 916. The cleaning device further includes a dual locking mechanism to prevent the cup-shaped flap 912 and the entrance flap 914 from opening during the wash cycle.

The cleaning chamber 910 may include a circular manifold with multiple spray nozzles 954 for spraying the medical instrument 930 and the interior of the cleaning chamber 910. An cleaning solution supply pipe or tube is connected to the manifold and spray nozzles 954 to supply a cleaning solution to the manifold and spray nozzles 954 such that the medical instrument 930 and the cylinder interior are decontaminated. The spray nozzles 954 may spray a fine mist into the cleaning chamber 910 to decontaminate the exterior of the medical instrument 930. A drain pipe coupled to the cup-shaped flap 912 allows accumulated liquid to drain from a bottom of the cleaning chamber 910 such that the cleaning solution is removed from the cleaning chamber 910 without the cylinder becoming filled. The drain pipe also drains the solution into the secondary wash cycle reservoir 952 to be reused during the cleaning cycle.

The secondary wash cycle reservoir 952 is connected by a pipe to the manifold. A wash cycle pump 950 coupled to the secondary wash cycle reservoir 952 delivers antimicrobial cleaning solution to the spray nozzles 954. The debris filter may be disposed between the secondary wash cycle reservoir 952 and the pump 950. This configuration allows debris to accumulate in the wash reservoir and then be dumped to the waste fluid reservoir 940 when a plug is opened. The secondary wash cycle reservoir 952 also includes a return pipe connected to the cup-shaped flap 912 to receive the fluid for recycling for the duration of the wash cycle. The secondary wash cycle reservoir 952 may include a level detection sensor to measure the required quantity of cleaning solution and collected solution to be reused multiple times during the wash cycle.

The secondary wash cycle reservoir 952 holds a measured quantity of cleaning solution that is sufficient for one cleaning or wash cycle, which one cleaning cycle is the cycle for cleaning one medical device or instrument. The wash cycle pump 950 takes the cleaning solution from the bottom of the secondary wash cycle reservoir 952 and feeds the cleaning solution through a first pipe to the at least one spray nozzle 952 located in the cleaning chamber 910. A second pipe returns run-off cleaning solution from the bottom of the cleaning chamber 910 back to the secondary wash cycle reservoir 852 for reuse during the cleaning or wash cycle. The secondary wash cycle reservoir 952 may also have an outlet to allow the disposal of used cleaning solution to the waste fluid reservoir 940 at the end of the wash cycle. The outlet may also serve as an overflow outlet in the event of unintentional overfilling of the secondary wash cycle reservoir 952. A filter (e.g., made of a fine mesh material) may be located at the inlet to the wash cycle pump 950 to prevent debris from being pumped into the spray nozzles 954 and causing blockages. The filter may be located such that any debris collection on the filter is cleared when the used cleaning solution is disposed of to the waste fluid reservoir 940.

In an embodiment, the cleaning solution may be a blend of water, microbial disinfectants, and detergents. In another embodiment, a cleaning solution concentrate may be used. The pump 950 connected to the secondary wash cycle reservoir 952 may dilute and mix the cleaning solution concentrate with clean water before pumping the mixture to the spray nozzles 954. In still another embodiment, a mixing region may be included for receiving an antimicrobial, sterilant, or disinfectant concentrate in either liquid or dry form. The mixing region may be connected with the pump 950 to mix the solution as the pump 950 pumps water from a water source.

The automatic cleaning system 900 also includes a microprocessor based controller, which controls all operations of the cleaning system 900 and is housed in the electronics housing 970. A remote command is issued to the controller through a communications system, which commands the automatic cleaning system 900 to dispense the medical instrument 930.

The medical instrument 930 is dispensed from the cleaning chamber 910 by the motor pulley mechanism, which delivers the medical instrument 930 to within an arm's reach of the user. The user grasps the medical instrument 930 and pulls it towards the position for its designated use, and the drag clutch 926 controls the force required by the user to pull out the additional cable 922 or additional portion of the cable 922. The controller is configured to determine the deployment distance required to lower the medical instrument 930 to make it available for use. The controller is also configured to allow the user to easily pull additional cable 922 from the cable spool 920 to allow the medical instrument 930 to be used at an increased distance from it deployment position.

Excess cable 922 may be taken up by a winch, which has a system to commute power and data to and from external power and communication. Excess cable 922 may be and wound around the cable spool 920. Excess cable 922 may also be routed over the top of the cleaning chamber 910 and may be driven over an idler pulley to form a "U" shaped loop of cable in a cable shaft. One end of the cable 922 may be connected to the medical instrument 930 and the other end of the cable 922 may be connected to external power and communications.

During use of the medical instrument 930, power and data from the medical instrument 930 are carried through the cable 922 to the controller and then relayed back to a medical practitioner at the MCC 104 (in a location separate from the tele-health cabin 106). During use, the medical instrument 930 will likely become soiled and contaminated when handled by the user.

The medical practitioner will determine when the use of the medical instrument 930 is complete. The medical practitioner may make this determination by observing the user via a simultaneous video conference link, and may at the appropriate time issue a remote command to the controller to retract the medical instrument 930 into the cleaning chamber 910. The drag clutch 926 limits the retraction force to prevent snatching of the medical instrument 930 from the hand of the user.

The controller retracts the medical instrument 930 to the top of the cleaning chamber 910 where a sensor 932 detects this fully retracted position, which is referred to later as the "home position." The controller is configured to detect when the medical instrument 930 is fully retracted into the cleaning chamber 910. The controller then closes the upper cup-shaped flap 912 followed by the lower entrance flap 914. The controller then activates a double cam lock, which is mechanized to lock both the upper and lower flaps 912 and 914 closed. Closure of the upper flap 912 seals the bottom of the cleaning chamber 910 and the lower flap 914 prevents user access to the cleaning device.

The cleaning process is then initiated by the controller at the appropriate time.

The automatic cleaning system 900 includes a primary reservoir 930. The large primary reservoir is a tank which can hold sufficient clean wash fluid or cleaning solution 932 for multiple medical instrument cleaning cycles. The primary reservoir 930 may include a low level sensor 934, which is used to alert maintenance personnel when the clean wash fluid 932 needs to be replenished, and an empty level sensor, which is used to inhibit cleaning system operation when there is insufficient clean wash fluid 932 for a wash cycle. The primary reservoir 930 may be located below the cleaning device to prevent unwanted syphoning of clean wash fluid 932. The primary reservoir 930 also includes an opening 936 through which the clean wash fluid 932 may be refilled or replenished.

The automatic cleaning system 900 also includes the secondary reservoir 952. The small secondary reservoir 952 may be located within the cleaning device and below the cleaning chamber 910. The secondary reservoir 952 may include an overflow system (e.g., tube, chamber, container, pot) disposed therein to allow excess clean wash fluid 932 to escape in the event of a malfunction. The secondary reservoir 952 may include a plug, which is mechanically operated via a push rod and is used to close or open an outlet drain hole disposed at the bottom of the secondary reservoir 952. The secondary reservoir 952 has a pump 950 which pumps fluid from the secondary reservoir 952 through tubes into the spay nozzles 954 within the cleaning chamber 910. The secondary reservoir 952 has a return tube which connects from the bottom of the upper cup-shaped flap 912 to the top of the secondary reservoir 952.

To fill the secondary reservoir 952, the controller closes the secondary reservoir outlet drain with the plug and then uses the pump 950 to transfer clean wash fluid 932 from the primary reservoir 930 via a tube to the secondary reservoir 952. The secondary reservoir 952 has a high level fluid sensor which is used to measure a clean wash fluid dosage. Extensive functional trials were carried out to determine the optimal dosage require to clean each medical instrument thoroughly.

The automatic cleaning system 900 further includes a waste fluid reservoir 940 to store used cleaning fluid 942 for later disposal. This waste fluid reservoir 940 includes a high level fluid sensor 944 to alert maintenance personnel when the waste wash fluid reservoir 940 is nearly full and needs to be emptied, and a full level fluid sensor which inhibits cleaning system operation to prevent waste fluid reservoir overflow. The waste fluid reservoir 940 includes an opening 946 through which the waste wash fluid 942 may be emptied.

The automatic cleaning system 900 may further include an air drying system 960. The air drying system includes an intake fan 962 though which room temperature air flow into the air drying system 960. Optionally, the air drying system 960 may include a heater to warm up the room temperature air. Ducts (e.g., air duct 964) of the air drying system 960 carry warm and room temperature air to the cleaning chamber 910 to dry the medical instrument 930 and the inside of the cleaning chamber 910 at the end of the wash cycle. Ducts also direct exhaust air away from the cleaning chamber 910.

The drip tray 916 has a gutter, which collects waste and any spills or run off from the cleaning device. The gutter routes the collected waste, spills, or run off to the waste fluid reservoir 940 for disposal.

In an embodiment, the microprocessor based controller is programmed to carry out the following steps in a cleaning cycle: deliver the medical instrument 930 to within arms-reach of the user; measure an amount of cleaning solution required to clean the medical instrument 930; determine whether the medical instrument 930 has been used and requires cleaning; determine when to retract the medical instrument 930 to a predetermined location at the top of the cleaning chamber 910; determine whether the medical instrument 930 is at the home position in the cleaning chamber 910; check whether the primary reservoir 930 (clean wash fluid reservoir) has sufficient quantity of clean wash fluid 932 for a wash cycle; check whether waste reservoir 940 has sufficient capacity to hold the waste from a wash cycle; close and lock upper and lower flaps 912 and 914 of the cleaning chamber 910 and drip plate 916; close plug on the secondary reservoir outlet drain; pump clean wash fluid 932 from primary reservoir 930 to secondary reservoir 952 until the high level fluid sensor in the secondary reservoir 952 is triggered; and start cleaning pump 950, which pumps wash fluid 932 from the secondary reservoir 952 to the spray nozzles 954 in the cleaning chamber 910.

The spray nozzles 954 spray a mist of cleaning fluid over the medical instrument 930. Fluid running off collects at the bottom of the cleaning chamber 910 into the cup shaped flap 912. The fluid run off drains into the secondary reservoir 952 for reuse during the current cleaning cycle.

During the cleaning process, the medical instrument 930 is cycled or moved up and down by the motor pulley arrangement to distribute cleaning fluid over the medical instrument 930 to enhance the cleaning process. The controller is configured to determine the maximum distance that the medical instrument 930 can be lowered within the cleaning chamber 910 without contacting the cup-shaped flap 912. Algorithms based on the size and shape of the medical instrument 930 may be used to provide the optimal up and down cycling motion. Algorithms based on the size and shape of the medical instrument 930 may also be used to determine the duration of the wash cycle.

At the end of the wash cycle, the cleaning pump 950 is stopped and the plug on the secondary reservoir outlet drain is opened to allow the used cleaning fluid to drain through the gutter in the drip tray 916 into the waste fluid reservoir 940. Once the waste solution is drained away, the air drying system 960 is activated. The medical instrument 930 is dried using warm air. Algorithms may be used to determine the duration of the dry cycle based on the size and shape of the medical instrument 930. Towards the completion of the drying cycle, room temperature air is used to cool the medical instrument 930 and the cleaning chamber 910. The medical instrument 930 is now clean and available for reuse.

Optionally, the dry cycle may include the use of ultra violet lights mounted in the lid 928 or at the side of the cleaning chamber 910 to enhance the sterilization of the medical instrument 930.

In an embodiment, the medical instrument 930 may be capable of being sprayed with pressurized antimicrobial cleaning solution without sustaining any harm, typically IEC IP66 rating or better. In some embodiments, it may be desirable to use suction to draw air through the cleaning chamber 910. This offers two advantages: 1) a negative pressure is created within the cleaning chamber 910 preventing any leakage, and 2) reduced pressure would aid evaporation.

FIGS. 11-15 are flowcharts illustrating a method of operating an automatic cleaning system, according to an embodiment.

Figure 11:
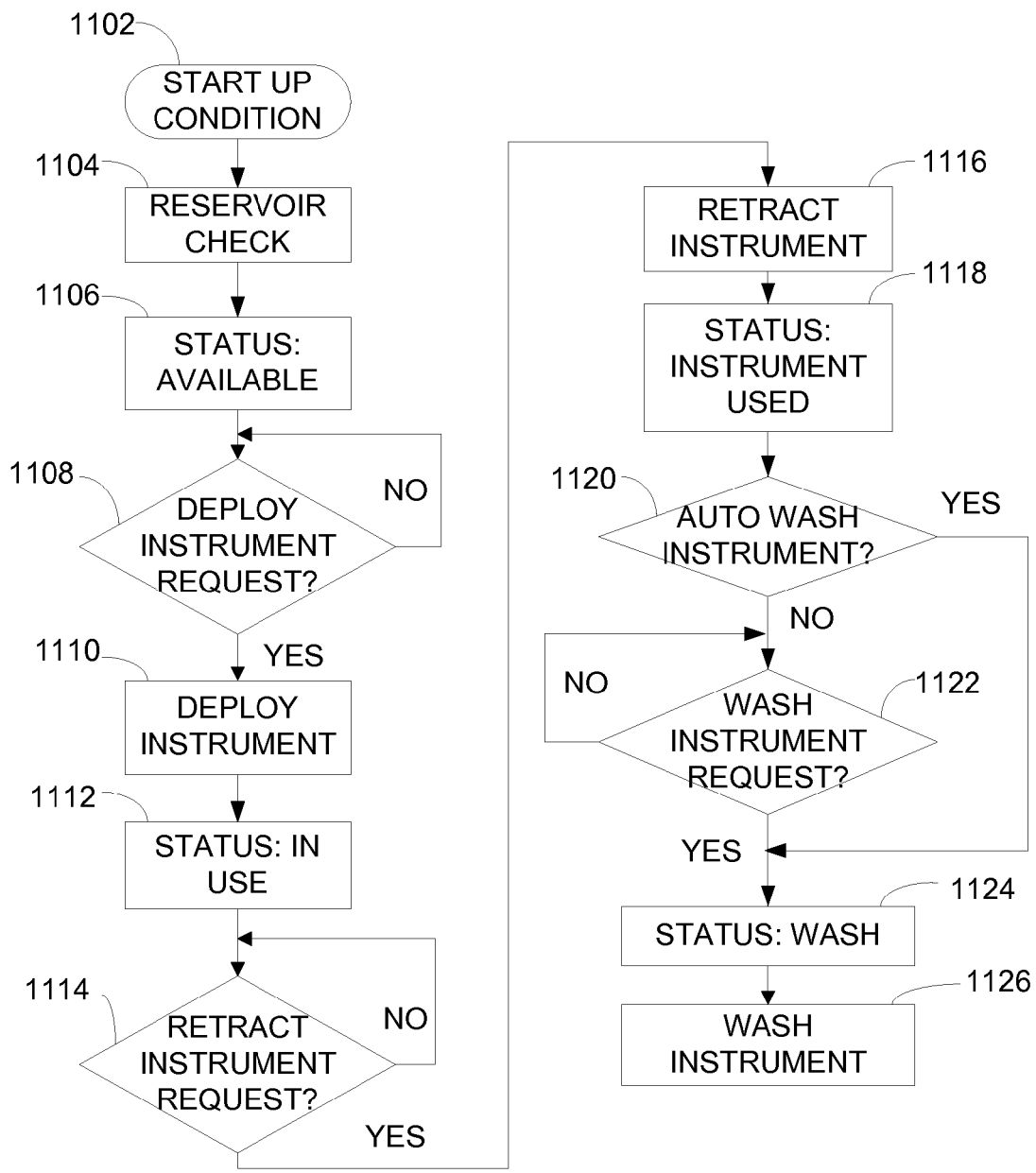
FIGS. 11-15 are flowcharts illustrating a method of operating an automatic cleaning system, according to an embodiment.

FIG. 11 is a flowchart illustrating an overview of the method of operating the automatic cleaning system, according to an embodiment. At step 1102, then cleaning system determines whether its startup conditions have been met. The cleaning system determines whether the medical instrument is retracted to the "home" position inside the cleaning chamber, whether the first and second flaps are closed and locked, whether a drain plug in the wash cycle reservoir (e.g., the secondary reservoir 952) is open, whether the clean solution reservoir is full, and whether the waste solution reservoir is empty.

At step 1104, the cleaning system checks the status of the reservoirs and updates the status of the cleaning system to "available" at step 1106. The cleaning system then determines whether a request to deploy the medical instrument has been received at step 1108. If the deployment request has been issued (YES of step 1108), then the cleaning system deploys the medical instrument at step 1110. If the deployment request has not been issued (NO of step 1108), then the process returns to the step 1108 to wait for a deployment request.

At step 1112, the cleaning system updates its status to "in use." The cleaning system then determines whether a request to retract the medical instrument has been received at step 1114. If the retract request has been issued (YES of step 1114), then cleaning system retracts the medical instrument at step 1116. If the retract request has not been issued (NO of step 1114), then the process returns to step 1114 to wait for a retract request.

After retracting the medical instrument, the cleaning system updates its status to "instrument used." At step 1120, the cleaning system determines whether the automatic wash instrument command has been set. If the automatic wash instrument command has been set (YES of step 1120), then the cleaning system sets its status to "wash" at step 1124 and washes the medical instrument at step 1126. If the automatic wash instrument command has not been set (NO of step 1120), then then cleaning system determines whether a wash instrument request has been transmitted or received at step 1122. If a wash instrument request has been received (YES of step 1122), then the cleaning system sets its status to "wash" at step 1124 and washes the medical instrument at step 1126. If a wash instrument request has not been received (NO of step 1122), the process returns to step 1122 to wait for a wash instrument request.

Figure 12:
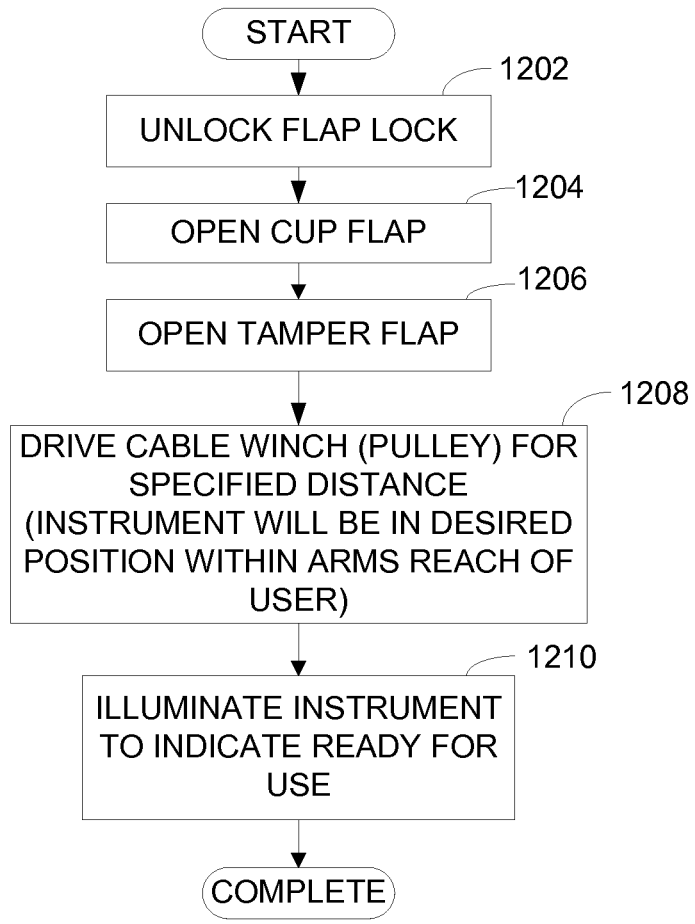

FIG. 12 is a flowchart illustrating a method of deploying the medical instrument in the automatic cleaning system, according to an embodiment. At step 1202, the cleaning system unlocks the locks to the first flap (cup flap) of the cleaning chamber and the second flap (tamper flap) of the base plate. The cleaning system then opens the cup flap at step 1204 and opens then tamper flap at step 1206. At step 1208, the cleaning system drives the cable winch (pulley) for a specified or predetermined distance, so that the medical instrument will be in a desired position of within an arm's reach of a user. Once the medical instrument has been deployed from the cleaning chamber, the cleaning system may illuminate the medical instrument to indicate to the user that the instrument is ready for use at step 1210.

Figure 13:
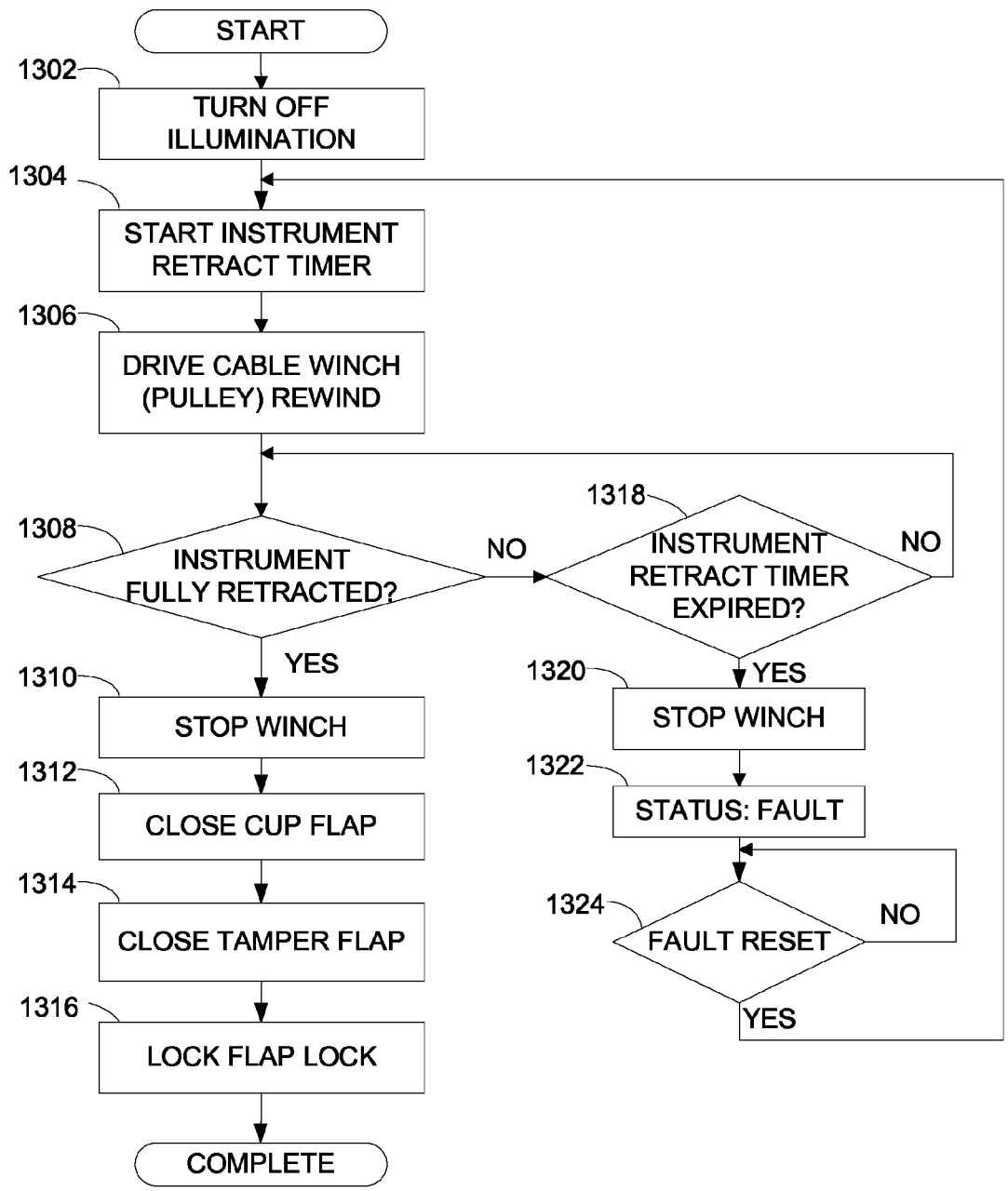

FIG. 13 is a flowchart illustrating a method of retracting the medical instrument in the automatic cleaning system, according to an embodiment. At step 1302, the cleaning system turns off the illumination of the medical instrument. The cleaning system then starts an instrument retract timer at step 1304. At step 1306, the cleaning system drives the cable winch (pulley) to rewind the cable that is coupled to the medical instrument. At step 1308, the cleaning system determines whether the medical instrument has been fully retracted (e.g., retracted to the "home" position in the cleaning chamber). If the medical instrument has been fully retracted (YES of step 1308), the cleaning system then stops the cable winch at step 1310. The cleaning system closes the cup flap at step 1312 and closes the tamper flap at step 1314. Then in step 1316, the cleaning system locks the cup flap and the tamper flap closed.

If the cleaning system determines that the medical instrument has not been fully retracted (NO of step 1308), the cleaning system then determines whether the instrument retract timer has expired at step 1318. If the instrument retract timer has not expired (NO of step 1318), the process returns to step 1308 to determine whether the instrument has been fully retracted. If the instrument retract timer has expired (YES of step 1318), the cleaning system stops the cable winch at step 1320 and sets its status to "fault" at step 1322. When the status of the cleaning system is "fault," the cleaning system may send an alert to the user, the medical personnel at the remote MCC, or a maintenance personnel to check the status of the cleaning system and perform any necessary maintenance. The user, the medical personnel or the maintenance personnel may reset the "fault" status at step 1324 (YES) so that the cleaning system may return to normal operation at step 1304. If the "fault status" is not reset (NO of step 1324), the cleaning system will remain in the "fault" status.

Figure 14:
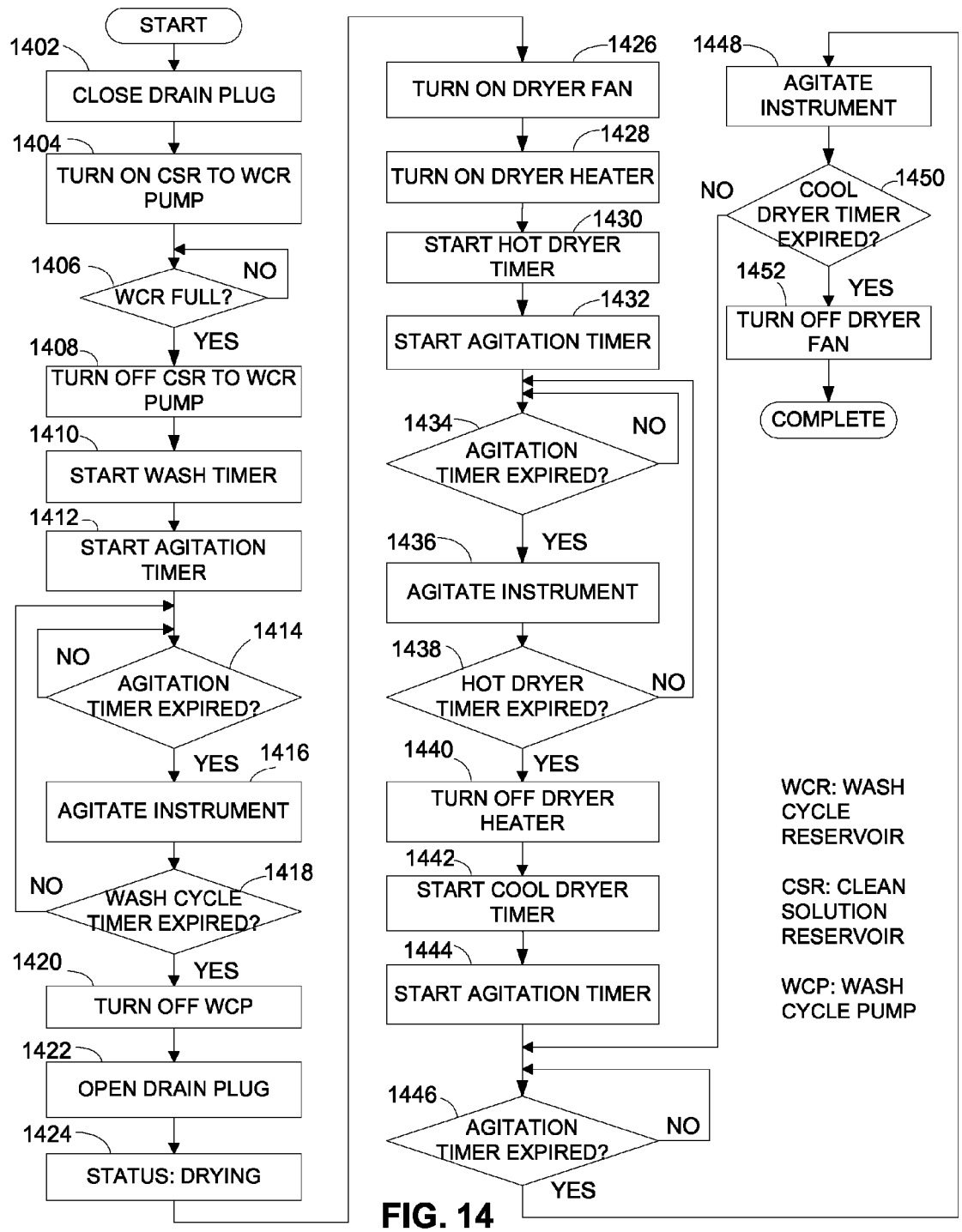

FIG. 14 is a flowchart illustrating a method of washing the medical instrument in the automatic cleaning system, according to an embodiment. At step 1402, the cleaning system closes the drain plug in the wash cycle reservoir. At step 1404, the cleaning system turns on the cleaning solution pump, which pumps cleaning solution from the clean solution reservoir (CSR) to the wash cycle reservoir (WCR). At step 1406, the cleaning system checks whether the wash cycle reservoir is full. If the wash cycle reservoir is full (YES of step 1406), the cleaning system turns off the wash cycle pump. If the wash cycle reservoir is not full (NO of step 1406), the cleaning solution pump then continues to pump cleaning solution from the clean solution reservoir to the wash cycle reservoir.

Once the wash cycle reservoir is full, the cleaning system starts the wash cycle timer at step 1410 and the agitation timer at step 1412. At step 1414, the cleaning system determines whether the agitation timer has expired. If the agitation timer has expired (YES of step 1414), the cleaning system agitates the medical instrument (e.g., cycles the medical instrument up and down) in the cleaning chamber at step 1416 for the wash cycle. If the agitation timer has not expired (NO of step 1414), the cleaning system waits for the agitation timer to expire.

The cleaning system agitates the medical instrument for the remainder of the wash cycle timer and determines whether the wash cycle timer has expired at step 1418. If the wash cycle timer has expired (YES of step 1418), then at step 1420, the cleaning system turns off the wash cycle pump (WCP), which has been pumping cleaning solution from the wash cycle reservoir to the at least one spray nozzle in the cleaning chamber. If the wash cycle timer has not expired (NO of step 1418), the process returns to step 1414.

Next, the cleaning system opens the drain plug to the wash cycle reservoir at step 1422 and sets its status to "drying" at step 1424. The cleaning system then turns on the dryer fan at step 1426 and turns on the dryer heater at 1428. At step 1430, the cleaning system starts the hot dryer timer. Then at step 1432, then cleaning system starts the agitation timer again. At step 1434, the cleaning system determines whether the agitation timer has expired. If the agitation timer has expired (YES of step 1434), the cleaning system agitates the medical instrument in the cleaning chamber at step 1436 for the drying cycle. If the agitation timer has not expired (NO of step 1434), the cleaning system waits for the agitation timer to expire.

The cleaning system agitates the medical instrument for the remainder of the hot dryer timer and determines whether the hot dryer timer has expired at step 1438. If the hot dryer timer has expired (YES of step 1438), then at step 1440, the cleaning system turns off the dryer heater, which has been supplying heated air to the cleaning chamber to dry the medical instrument. If the hot dryer cycle has not expired (NO of step 1438), the process returns to step 1434.

At step 1442, the cleaning system starts the cool dryer timer. The cleaning system again starts the agitation timer at step 1444. The cleaning system determines whether the agitation timer has expired in step 1446. If the agitation timer has expired (YES of step 1446), the cleaning system agitates the medical instrument at step 1448. If the agitation timer has not expired (NO of step 1446), then the cleaning system waits for the agitation timer to expire. At step 1450, the cleaning system determines whether the cool dryer timer has expired. If the cool dryer timer has not expired (NO of step 1450), the process returns to step 1446. If the cool dryer timer has expired (YES of step 1450), then at step 1452, the cleaning system turns off the dryer fan, which has been supplying cool air or ambient temperature air to the cleaning chamber to dry the medical instrument.

Figure 15:
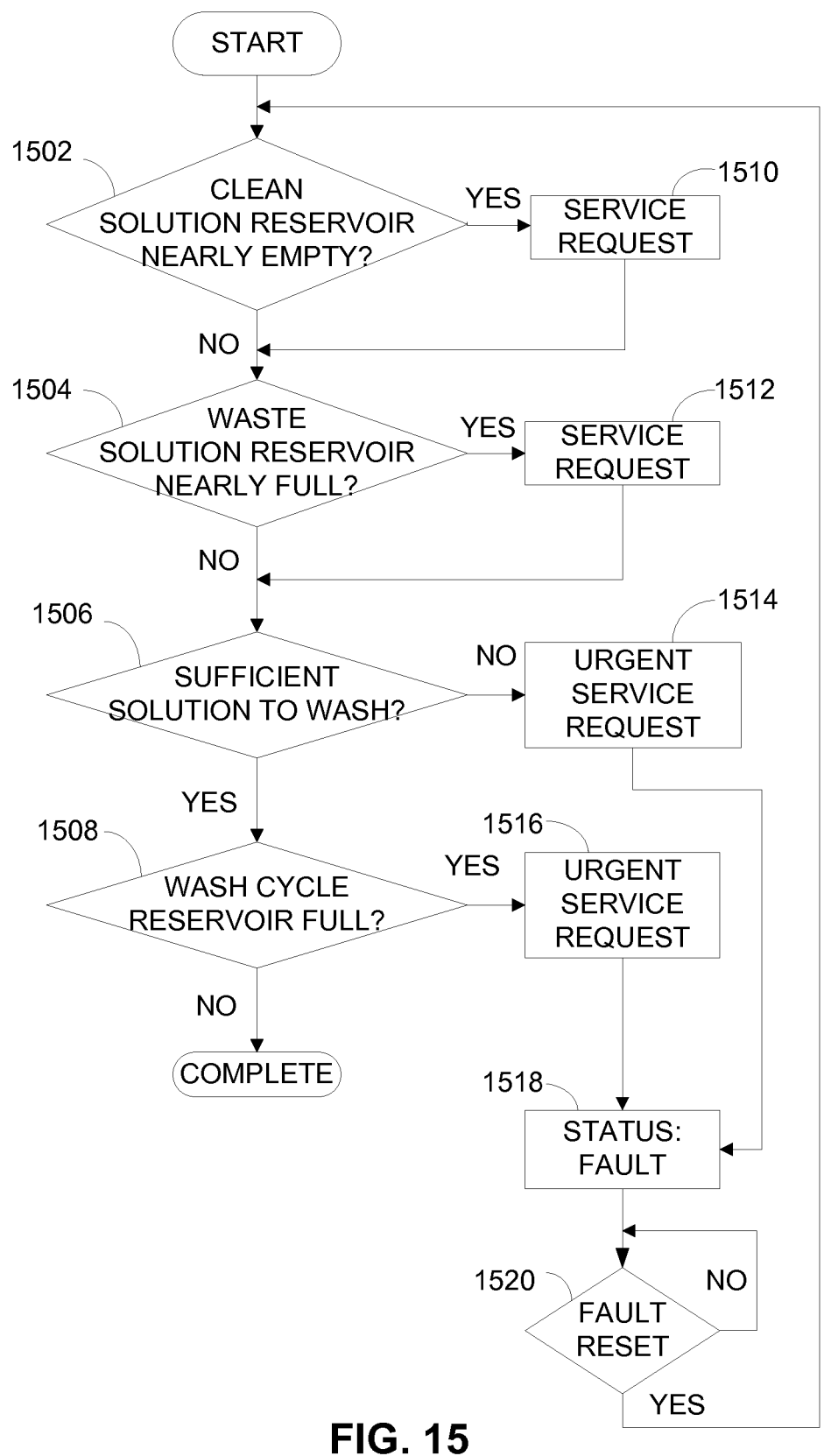

FIG. 15 is a flowchart illustrating a method of checking the reservoir status in the automatic cleaning system, according to an embodiment. At step 1502, the cleaning system checks whether the clean solution reservoir is nearly empty. If the clean solution reservoir is not nearly empty (NO of step 1502), the cleaning system checks whether the waste solution reservoir is nearly full at step 1504. If the waste solution reservoir is not nearly full (NO of step 1504), the cleaning system checks whether the clean solution reservoir contains sufficient clean cleaning solution to wash a medical instrument at step 1506. If there is sufficient clean cleaning solution (YES of step 1506), then the cleaning system checks whether the wash cycle reservoir is full at step 1508. If the wash cycle reservoir is not full (NO of step 1508), i.e., the wash cycle reservoir was emptied after a previous wash cycle, then the status check process is complete.

However, if the clean solution reservoir is nearly empty (YES of step 1502) or if the waste solution reservoir is nearly full (YES of step 1504), the cleaning system sends a service request at steps 1510 or 1512 to the maintenance personnel. The maintenance personnel may then refill the cleaning solution reservoir or empty the waste solution reservoir. If the cleaning system determines that the clean solution reservoir does not contain sufficient clean cleaning solution (NO of step 1506), the cleaning system then sends an urgent service request to the maintenance personnel at step 1514 and then sets its status to "fault" at step 1518. Similarly, if the cleaning system determines that the wash cycle reservoir is full (YES at step 1508), i.e., the wash cycle reservoir was not emptied after a previous wash cycle, the cleaning system then sends an urgent service request to the maintenance personnel at step 1516 and then sets its status to "fault" at step 1518. The maintenance personnel may reset the status of the cleaning system at step 1520 once the clean solution reservoir is refilled or once the wash cycle reservoir is emptied. Otherwise, the cleaning system will remain in a "fault" status until maintenance is performed.

In another embodiment, a plurality of the automatic cleaning systems may be used in the tele-health cabin 106. In the plurality of cleaning systems, as may be used in the tele-health cabin 106, additional functionality and the sharing of resources are explained as follows.

The plurality of cleaning systems can accommodate a plurality of individual medical instruments, and each of the individual medical instruments can be dispensed to the user. Furthermore, the cleaning process is only carried out on medical instruments that have been used during the examination session.

The primary reservoir 930 may be fitted with multiple pumps or valves connected to multiple secondary reservoirs. The empty level sensor may be positioned in the primary reservoir such that the primary reservoir has sufficient fluid is available to wash all of the medical instruments. The full level sensor may be positioned in the waste fluid reservoir such that the waste reservoir has sufficient capacity for the waste fluid from all of the medical instruments. Multiple secondary reservoirs may drain into a common gutter.

The warm and room temperature drying air is carried into a first manifold which delivers the drying air to the multiple cleaning chambers. The exhaust drying air also exits from each cleaning chamber into a second common manifold. Butterfly flaps are provided on the entry and or exit ducts to each individual cleaning chamber to prevent air entering cleaning chambers that have not washed.

All references, including publications, patent applications, and patents, cited herein are hereby incorporated by reference to the same extent as if each reference were individually and specifically indicated to be incorporated by reference and were set forth in its entirety herein.

For the purposes of promoting an understanding of the principles of the invention, reference has been made to the embodiments illustrated in the drawings, and specific language has been used to describe these embodiments. However, no limitation of the scope of the invention is intended by this specific language, and the invention should be construed to encompass all embodiments that would normally occur to one of ordinary skill in the art. The terminology used herein is for the purpose of describing the particular embodiments and is not intended to be limiting of exemplary embodiments of the invention. In the description of the embodiments, certain detailed explanations of related art are omitted when it is deemed that they may unnecessarily obscure the essence of the invention.

The apparatus described herein may comprise a processor, a memory for storing program data to be executed by the processor, a permanent storage such as a disk drive, a communications port for handling communications with external devices, and user interface devices, including a display, touch panel, keys, buttons, etc. When software modules are involved, these software modules may be stored as program instructions or computer readable code executable by the processor on a non-transitory computer-readable media such as magnetic storage media (e.g., magnetic tapes, hard disks, floppy disks), optical recording media (e.g., CD-ROMs, Digital Versatile Discs (DVDs), etc.), and solid state memory (e.g., random-access memory (RAM), read-only memory (ROM), static random-access memory (SRAM), electrically erasable programmable read-only memory (EEPROM), flash memory, thumb drives, etc.). The computer readable recording media may also be distributed over network coupled computer systems so that the computer readable code is stored and executed in a distributed fashion. This computer readable recording media may be read by the computer, stored in the memory, and executed by the processor.

Also, using the disclosure herein, programmers of ordinary skill in the art to which the invention pertains may easily implement functional programs, codes, and code segments for making and using the invention.

The invention may be described in terms of functional block components and various processing steps. Such functional blocks may be realized by any number of hardware and/or software components configured to perform the specified functions. For example, the invention may employ various integrated circuit components, e.g., memory elements, processing elements, logic elements, look-up tables, and the like, which may carry out a variety of functions under the control of one or more microprocessors or other control devices. Similarly, where the elements of the invention are implemented using software programming or software elements, the invention may be implemented with any programming or scripting language such as C, C++, JAVA®, assembler, or the like, with the various algorithms being implemented with any combination of data structures, objects, processes, routines or other programming elements. Functional aspects may be implemented in algorithms that execute on one or more processors. Furthermore, the invention may employ any number of conventional techniques for electronics configuration, signal processing and/or control, data processing and the like. Finally, the steps of all methods described herein may be performed in any suitable order unless otherwise indicated herein or otherwise clearly contradicted by context.

For the sake of brevity, conventional electronics, control systems, software development and other functional aspects of the systems (and components of the individual operating components of the systems) may not be described in detail. Furthermore, the connecting lines, or connectors shown in the various figures presented are intended to represent exemplary functional relationships and/or physical or logical couplings between the various elements. It should be noted that many alternative or additional functional relationships, physical connections or logical connections may be present in a practical device. The words "mechanism", "element", "unit", "structure", "means", and "construction" are used broadly and are not limited to mechanical or physical embodiments, but may include software routines in conjunction with processors, etc.

The use of any and all examples, or exemplary language (e.g., "such as") provided herein, is intended merely to better illuminate the invention and does not pose a limitation on the scope of the invention unless otherwise claimed. Numerous modifications and adaptations will be readily apparent to those of ordinary skill in this art without departing from the spirit and scope of the invention as defined by the following claims. Therefore, the scope of the invention is defined not by the detailed description of the invention but by the following claims, and all differences within the scope will be construed as being included in the invention.

No item or component is essential to the practice of the invention unless the element is specifically described as "essential" or "critical". It will also be recognized that the terms "comprises," "comprising," "includes," "including," "has," and "having," as used herein, are specifically intended to be read as open-ended terms of art. The use of the terms "a" and "an" and "the" and similar referents in the context of describing the invention (especially in the context of the following claims) are to be construed to cover both the singular and the plural, unless the context clearly indicates otherwise. In addition, it should be understood that although the terms "first," "second," etc. may be used herein to describe various elements, these elements should not be limited by these terms, which are only used to distinguish one element from another. Furthermore, recitation of ranges of values herein are merely intended to serve as a shorthand method of referring individually to each separate value falling within the range, unless otherwise indicated herein, and each separate value is incorporated into the specification as if it were individually recited herein.

What is claimed is:

1. A tele-health services cabin comprising:
    a patient chair comprising:
        a motorized seat back,
        a plurality of stethoscope sensors encapsulated in the seat back;
        a switch matrix connected to the plurality of stethoscope sensors;
        a block having a plurality of openings and configured to shield the plurality of stethoscope sensors from interference, wherein each of the plurality of stethoscope sensors is disposed proximate to an opening of the plurality of openings so as to detect audio signals from a patient's back through the opening;
    a processor that communicates with a remote medical call center via a bi-directional communication link, wherein the processor carries out steps comprising:
        under the control of a remote practitioner at a remote medical call center, activating, via the switch matrix, at least one stethoscope sensor of the plurality of stethoscope sensors;
        receiving audio signals from the activated stethoscope sensor;
        transmitting the audio signals over the communication link to the remote medical call center, wherein remote practitioner accesses the audio signals; and
    videoconferencing hardware via which the remote practitioner in the medical call center videoconferences with the patient in the cabin to diagnose symptoms of the patient.

2. The tele-health services cabin of claim 1, wherein the motorized seat back comprises an actuator that is remotely controllable from the medical call center via the communication link to move the plurality of sensors.

3. The tele-health services cabin of claim 1, wherein at any given moment, only one stethoscope sensor of the plurality of stethoscope sensors is energized to transmit audio signals of the patient's lungs to the medical call center.

4. The tele-health services cabin of claim 1, further comprising a height measurement device that comprises an ultrasonic sensor.

5. The tele-health services cabin of claim 4, wherein the ultrasonic sensor is remotely controlled from the medical call center.

6. The tele-health service cabin of claim 4, wherein the ultrasonic sensor is embedded in a portion of the ceiling above the patient chair.

* * * * *